US005861255A

United States Patent [19]
DeMuth et al.

[11] Patent Number: 5,861,255
[45] Date of Patent: *Jan. 19, 1999

[54] **COMPOSITION AND METHODS FOR DIAGNOSIS OF DISEASES ASSOCIATED WITH *ACTINOBACILLUS ACTINOMYCETEMCOMITANS* INFECTION**

[75] Inventors: Donald R. DeMuth, Drexel Hill; Edward T. Lally, West Chester, both of Pa.

[73] Assignee: The Trustees of the University of Pennsylvania, Philadelphia, Pa.

[*] Notice: The term of this patent shall not extend beyond the expiration date of Pat. No. 5,726,016.

[21] Appl. No.: 905,420

[22] Filed: Aug. 4, 1997

Related U.S. Application Data

[63] Continuation of Ser. No. 374,843, Jan. 18, 1995, Pat. No. 5,726,016.

[51] Int. Cl.[6] .............................. C12Q 1/68; C12P 19/34; C07H 21/04
[52] U.S. Cl. .............................. 435/6; 435/912; 536/287; 536/24.32; 536/24.1; 536/24.33; 935/8; 935/17; 935/78
[58] Field of Search .................... 435/6, 91.2; 536/23.7, 536/24.1, 24.32, 24.33; 935/8, 17, 78

[56] References Cited

U.S. PATENT DOCUMENTS

| | | | |
|---|---|---|---|
| 4,741,999 | 5/1988 | Genco et al. | 435/7 |
| 4,866,167 | 9/1989 | Chen et al. | 536/27 |
| 5,212,059 | 5/1993 | Schwartz et al. | 435/6 |
| 5,221,618 | 6/1993 | Klein et al. | 435/69.1 |
| 5,225,324 | 7/1993 | McFadden et al. | 435/6 |
| 5,258,284 | 11/1993 | Morris, Jr. et al. | 435/6 |
| 5,294,533 | 3/1994 | Lupski et al. | 435/6 |

FOREIGN PATENT DOCUMENTS

| | | |
|---|---|---|
| 3-175987 | 12/1989 | Japan . |
| WO 91/16455 | 10/1991 | WIPO . |
| WO 92/01815 | 2/1992 | WIPO . |
| WO 92/16630 | 10/1992 | WIPO . |

OTHER PUBLICATIONS

Baehni et al., "Leukotoxic Activity in Different Strains of the Bacterium *Actinobacillus actinomycetemcomitans* Isolated From Juvenile Periodontitis in Man", *Arch. Oral Biol.* 1981, 27, 671–676.

Block et al., "Actinobacillus actinomycetemcomitans Endocarditis: Report of a Case and Review of the Literature", *A. J. Med. Sci.* 1973, 276, 387–392.

Brogan, J. et al., "Regualtion of *Actinobacillus actinomycetemcomitans* Leukotoxin Expression: Analysis of the Promoter Regions of Leukotoxic and Minimally Leukotoxic Strains", *Infection and Immunity* 1994, 62(2), 501–508.

Collins et al. in, In vivo and in vitro erythropoiesis, the Friend system, Rossi, G.B., ed., Elsevier/North Holland Biomedical Press, NY, 1980.

Devereux, J. et al., "A Comprehensive Set of Sequence Analysis Programs for the VAX", *Nucl. Acids Res.* 1984, 12, 387–395.

Felmlee, T. and Welch, "Alterations of Amino Acid Repeats in the *Escherichia Coli* Hemolysin Affect Cytolytic Activity and Secretion", *PNAS USA* 1988, 85, 5279–5273.

Felmlee, T. et al., "Nucleotide Sequence of an *Escherichia coli* Chromosomal Hemolysin", *J. Bacteriol.* 1985, 163, 94–105.

(List continued on next page.)

*Primary Examiner*—Carla J. Myers
*Attorney, Agent, or Firm*—Panitch Schwarze Jacobs & Nadel, P.C.

[57] ABSTRACT

The invention features primers capable of distinguishing between highly toxic and minimally toxic strains of *Actinobacillus actinomycetemcomitans*, methods of detecting the presence of highly toxic and minimally toxic strains of *Actinobacillus actinomycetemcomitans* in samples obtained from a patient and kits for detection of the presence of highly toxic and minimally toxic strains of *Actinobacillus actinomycetemcomitans* in samples obtained from a patient.

4 Claims, 12 Drawing Sheets

```
<----------glyA(1260bp)---------->TAATTTTAATCAAATGAAAAAAAACA    -554

AAGCGGTAATGAAAATTGCCGCTTTTTCTTTTTGAGAAATATGACAGTCAAAATCTTACA   -494

---->< ----
GATCAAAACCTGATAACAGTATTTTCTCAGTCTAATTTTTGCGTATTAATACAATACGGG   -434

-------*--*-*-*-->   <--*-*-*--*------
ATTGCGTAGATAAAGTATTATCAAAAAACTAATAATTTTATGAAATTAAATAATTTTTTC   -374

-35           -10       ▼
     TATTGACTATTAAAGAATCCGGAGTAAATTAGTCTCCAAAATTAACCAAAACTAGGTAAT   -314
                                          RBS
     TTATCCGGTCAAAGGTTATCTTAAGTATTAACCCTAAGAAAAAGGAAAACGAGTATGTCC   -254
  1                                                       M  S

AGTACAGAATATGCTCCATTTTATCTCCGTTTTATTCAGTTCCCAAGTAATGAAGTTTTA   -194
  3   S  T  E  Y  A  P  F  Y  L  R  F  I  Q  F  P  S  N  E  V  L
                                   ----->< ------
     CTCTATGAATACTGGAAACTTGTTCAGAATTTTGTACAAAAGGTTAGTAAAATAACGGTA   -134
 23   L  Y  E  Y  W  K  L  V  Q  N  F  V  Q  K  V  S  K  I  T  V

AGATTAGCACAAATCGTTGGCATTCTCGGCGAAAAAACTATTTGGAAATACCAAAGTACT    -74
 43   R  L  A  Q  I  V  G  I  L  G  E  K  T  I  W  K  Y  Q  S  T
        -35        -10        ▼
     TTTAATGATGGCATGCTGGATATTGTGGTTTGGTTATCTTATTCAAAATAAATTATTAAC    -14
 63   F  N  D  G  M  L  D  I  V  V  W  L  S  Y  S  K  *
     RBS
```

OTHER PUBLICATIONS

Furste, J. et al., "Molecular Cloning of the Plasmid RP4 Primase Region in a Multi–Host–Range tacP Expression Vector" *Gene* 1986, 48, 119–131.

Goncharoff et al., "Identification of *Actinobacillus acitnomycetemcomitans:* Polymerase Chain Reaction Amplification of IktA–specific Sequences", *Oral.*

Guthmiller et al., "A Panel of Probes Detects DNA Polymorphisms in Human and Non–human Primate Isolates of a Periodontal Pathogen, *Actinobacillus actinomycetemcomitans*", *Microbiol. Pathog.* 1993, 14, 103–115.

Kraig, E. et al., "Nucleotide Sequence of the Leukotoxin Gene from *Actinobacillus actinomycetemcomitans:* Homology to the Alpha–Hemolysin/Leukotoxin Gene Family", *Infect. Immun.* 1990, 58, 920–929.

Lally et al., "Structure and Function of the B and D Genes of the *Actinobacillus actinomycetemcomitans* Leukotoxin Complex", *Microb. Pathog.* 1991, 11, 111–121.

Lally, E. et al., "Analysis of the *Actinobacillus actinomycetemcomitans* Leukotoxin Gene", *J. Biol. Chem.* 1989, 274, 15451–15456.

Lally, E. et al., "Identification and Expression of the *Actinobacillus actinomycetemcomitans* Leukotoxin Gene", *Biochem. Biophys. Res. Comm.* 1989, 159, 256–272.

Lalonde, G. et al., "Development of a Shuttle Vector and a Conjugative Transfer System for *Actinobacillus pleuropneumoniae*", *Gene* 1989, 85, 243–246.

Lin, C.-Y. et al., "Rapid and Specific Detection of the Leukotoxin Sequences of *Actinobacillus Actinomycetemcomitans* from Periodontal Pockets by the Polymerase Chain Reaction", *J. Formos Med. Assoc.* 1994, 93, 289–293.

Ludwig et al., "The Repeat Domain of *Escherichia coli* Haemolysin (HlyA) is Responsible for its $Ca^2$–Dependent Binding to Erythrocytes", *Mol. Gen. Genet.* 1988, 214, 553–561.

Ludwig, A. et al., "Mutations Affecting Activity and Transport of Haemolysin in *Escherichia coli*", *Mol. Gen. Genet.* 1987, 206, 238–245.

Page et al., "Infection Due to *Actinobacillus Actinomycetemcomitans* and *Haemophilus Aphrophilus*", *N. Engl. J. Med.* 1966, 275, 181–188.

Plamann, M. et al., "Complete Nucleotide Sequence of the *E. coli* gly A Gene", *Nucl. Acids. Res.* 1983, 11, 2065–2075.

Reddy et al., "Bacterial RNA Isolation with One Hour Centrifugation in a Table–Top Ultracentrifuge", *BioTechniques* 1990, 8, 250–251.

Sambrook et al., *Molecular Cloning: A Laboratory Manual.* Cold Spring Harbor, NY, 1989.

Sanger et al., "DNA Sequencing With Chain–Terminating Inhibitors", *PNAS USA* 1977, 74, 5463–5467.

Spitznagel, J. et al., "Regulation of Leukotoxin in Leukotoxic and Nonleukotoxic Strains of *Actinobacillus actinomycetemcomitans*", *Infect. Immun.* 1991, 59, 1394–1401.

Taichman et al., "Comparative Studeis on the Biology of *Actinobacillus actinomycetemcomitans* Leukotoxin in Primates", *Oral Microbiol. Immun.* 1987, 2, 97–104.

Taichman et al., "Cytopathic Effects of *Actinobacillus actinomycetemcomitans* on Monkey Blood Leukocytes", *J. Period. Res.* 1984, 19, 133–145.

Taichman, N. et al., "Biochemical and Morphological Characterization of the Killing of Human Monocytes by a Leukotoxin derived from *Actinobacillus actinomycetemcomitans*", *Infect. Immun.* 1980, 28, 258–278.

Tonjum, T. et al., "Identification of *Actinobacillus acitnomycetemcomitans* by Leukotoxin Gene–Specific Hybridization and Polymerase Chain Reaction Assays", *J. Clinical Microb.* 1993, 31, 1856–1859.

Welch, R., "Pore–forming Cytolysins of Gram–negative Bacteria", *Mol. Microb.* 1991, 5, 521–528.

Zambon, J. et al., "Serology of Oral *Actinobacillus actinomycetemcomitans* and Serotype Distribution in Human Periodontal Disease", *Infect. Immun.* 1983, 41, 19–27.

Zambon, "*Actinobacillus Actinomycetemcomitans* in Human Periodontal Disease", *J. Clin. Periodontal.* 1985, 12, 1–20.

Boehringor Mannheim Catalog, 1990/1991, p. 219.

Boehringer Mannheim Catalog, pp. 219 and 227, 1991.

FIGURE 1A

```
<--------glyA(1260bp)-------->TAATTTTAATCAAATGAAAAAAACA        -554

AAGCGGTAATGAAAATTGCCGCGCTTTTTCTTTTGAGAAATATGACAGTCAAAATCTTACA  -494

GATCAAAACCTGATAACAGTATTTTCTCAGTCTAATTTTTGCGTATTAATACAATACGGG   -434
                              ----*-*-*-*--->

ATTGCGTAGATAAAGTATTATCAAAAAACTAATAATTTTATGAAATTAAATAATTTTTTC   -374
                                          <--*-*-*-*----->
                                        ▸
                              -10
TATTGACTATATTAAAGAATCCGGAGTAAAATTAGTCTCCAAAATTAACCAAAACTAGGTAAT -314
    -35                       RBS

TTATCCGGTCAAAGGTTATCTTAAGTATTAACCCTAAGAAAAAGGAAAACGAGTATGTCC   -254
                                                        M  S
AGTACAGAATATGCTCCATTTTATCTCCGTTTTATTCAGTTCCCAAGTAATGAAGTTTTA   -194
 S  T  E  Y  A  P  F  Y  L  R  F  F  I  Q  F  P  S  N  E  V  L
                              ----><-----
CTCTATGAATACTGGAAACTTGTTCAGAATTTGTACAAAAGGTTAGTAAAATAACGGTA    -134
 L  Y  E  Y  W  K  L  V  Q  N  F  V  Q  K  V  S  K  I  T  V

AGATTAGCACAAATCGTTGGCATTCTCGGCGAAAAAACTATTTGGAAATACCAAAGTACT   -74
 R  L  A  Q  I  V  G  I  L  G  E  K  T  I  W  K  Y  Q  S  T
                              -10
TTTAATGATGGCATGCTGGATATTGTGGTTTGGTTATCTTATTCAAAATAAATTATTAAC   -14
 F  N  D  G  M  L  D  I  V  V  W  L  S  Y  S  K  *
    RBS
```

```
              AAGGAGATTTAATATGGA ---> ltxC
                    +5
                     M
```

FIGURE 6

```
     TTTTTGCGTATTAATACAATACGGAATTGCATAGATAAAGTATTATCAAAAAACTAATAA       -930
                             -35                     -10
     TTTTATGAAATTAAATAATTTTTTCTATTGACTATTAAAGAATCCGGAGTAAATTAGTCT       -870

CCAAAATTAACCAAAACTAGGTAATTTATCCGGTCAAAGGTTATCTTAAGTATTAACCCT       -810
                       RBS
     AAGAAAAAGGAAAACGAGTATGTCCGGTACAGAATATGCTCCATTTTATCTCCGTTTTAT       -750
1                      M   S   G   T   E   Y   A   P   F   Y   L   R   F   I

TCAGTTCCCAAGTAATGAAGTTTTACTCTATGAATACTGGAAACTTGTTCAGAATTTTGT       -690
15    Q   F   P   S   N   E   V   L   L   Y   E   Y   W   K   L   V   Q   N   F   V

ACAAAAGGTTAGTAAAATAACGGTAAGATTAGCACAAATCGTTGGCATTCTCGGCGAAAA       -630
35    Q   K   V   S   K   I   T   V   R   L   A   Q   I   V   G   I   L   G   E   K
                                    -35
     AACTATTTGGAAATACCAAAGTACTTTTAATGATGGCATGCTGGAAGGTGAAGCAGCTAA       -570
55    T   I   W   K   Y   Q   S   F   N   D   G   M   L   E   G   E   A   A   K

ACAAGAAGTTTCCCGCACTTTAAGAAGTAGTGCTTTACTTGTCGCAAGTGCCATAGTTAT       -510
75    Q   E   V   S   R   T   L   R   S   S   A   L   L   V   A   S   A   I   V   I

CCACTTTAAATCTAATTTTACCAACCTTCTTATACTGTCACAGATTACACAATATTGTAG       -450
95    H   F   K   S   N   F   T   N   L   L   I   L   S   Q   I   T   Q   Y   C   R

ACATCGCCCTAAACCTAAAAAAAGTAAATACTTCCCCCTCTACCTCTCTTGCTTATTACG       -390
115   H   R   P   K   P   K   K   S   K   Y   F   P   L   Y   L   S   C   L   L   R

CAGACGATTAACTGAATTTAAAATTACCCTTCTACCGTTGCCATGGGGCTAGCTGCTATA       -330
135   R   R   L   T   E   F   K   I   T   L   L   P   L   P   W   G   *

TAGCTATGAAGATCAAATCCCGGTTTTCATTGTAAATTTAAAAATATATAAGAAATAATC       -270

TGAAGCCGACTTTATTTTTACCCAACTACGAATCACTCATTTAAATTAAATAGGTTTATT       -210

ATGCAAAATAATAAAGCTTGAATATATTCCTGTAATATAAGGTTAAATAAGTTATATTTC       -150

TATTTATTGTTTAACAATAATAATTAAATCATAGTCTATTTGATTTCGTAATGAGTTTGG       -90
                                          -10
     CATTTCTGTCATGCGATCGTGTAAGTTATTTTGTATATTGTGGTTTGGTTATCTTATTC       -30
                       RBS
     AAAATAAATTATTAACAAGGAGATTTAATATG- ltxC                              +3
```

FIGURE 9

```
                                          Breakpoint
                       ↙
JP2      GCATGCTGGATATTGTGGTTTGGTTATCTTA
         : : : : : : : : : : : : : : : : : : : : : :
652      TTATTTTGTATATTGTGGTTTGGTTATCTTA ov1              CTATAACACCAAACCA ov4            GACCTATAACACCAAA
```

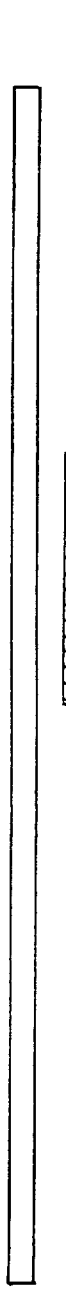
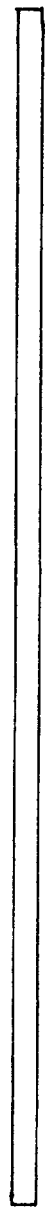
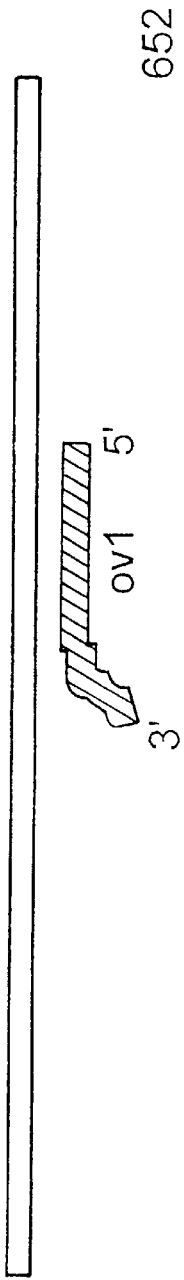
FIGURE 10A
FIGURE 10B

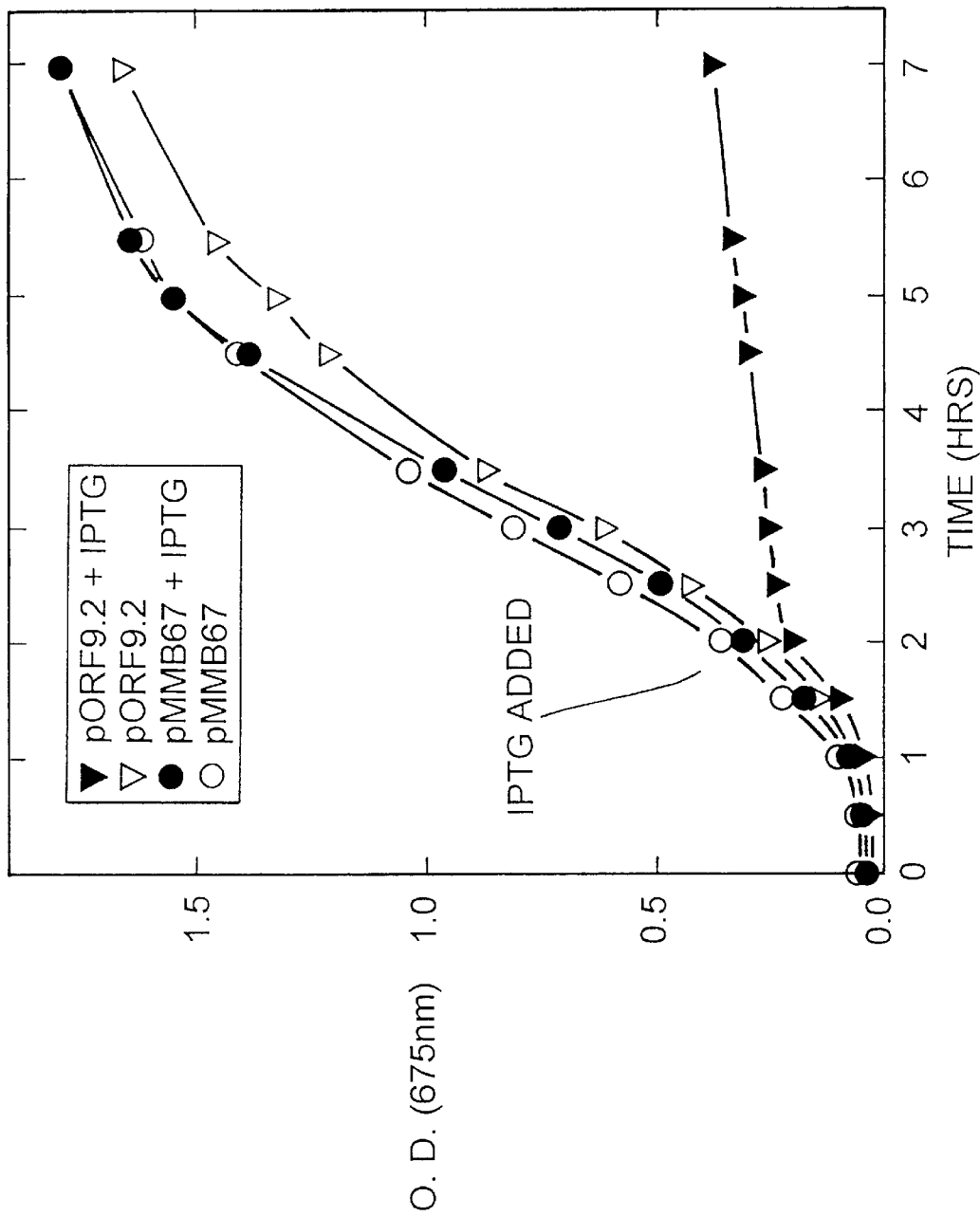

FIGURE 13

TAATTTTAATCAAATGAAAAAAAACAAAGCGGTAATGAAAATTGCCGCTTTTTCTTTTTGAGAAA
TATGACAGTCAAAATCTTACAGATCAAAACCTGATAACAGTATTTTCTCAGTCTAATTTTTGCGT
ATTAATACAATACGGGATTGCGTAGATAAAGTATTATCAAAAAACTAATAATTTTATGAAATTAA
ATAATTTTTTCTATTGACTATTAAAGAATCCGGAGTAAATTAGTCTCCAAAATTAACCAAAACTA
GGTAATTTATCCGGTCAAAGGTTATCTTAAGTATTAACCCTAAGAAAAAGGAAAACGAGTATGTC
CAGTACAGGATATGCTCCATTTTATCTCCGTTTTATTCAGTTCCCAAGTAATGAAGTTTTACTCT
ATGAATACTGGAAACTTGTTCAGAATTTTGTACAAAAGGTTAGTAAAATAACGGTAAGATTAGCA
CAAATCGTTGGCATTCTCGGCGAAAAAACTATTTGGAAATACCAAAGTACTTTTAATGATGGCAT
GCTGGATATTGTGGTTTGGTTATCTTATTCAAAATAAATTATTAACAAGGAGATTTAATATG

FIGURE 14

TTTTTGCGTATTAATACAATACGGAATTGCATAGATAAAGTATTATCAAAAAACTAATAATTTTA
TGAAATTAAATAATTTTTTCTATTGACTATTAAAGAATCCGGAGTAAATTAGTCTCCAAAATTAA
CCAAAACTAGGTAATTTATCCGGTCAAAGGTTATCTTAAGTATTAACCCTAAGAAAAAGGAAAAC
GAGTATGTCCGGTACAGAATATGCTCCATTTTATCTCCGTTTTATTCAGTTCCCAAGTAATGAAG
TTTTACTCTATGAATACTGGAAACTTGTTCAGAATTTTGTACAAAAGGTTAGTAAAATAACGGTA
AGATTAGCACAAATCGTTGGCATTCTCGGCGAAAAACTATTTGGAAATACCAAAGTACTTTTAA
TGATGGCATGCTGGAAGGTGAAGCAGCTAAACAAGAAGTTTCCCGCACTTTAAGAAGTAGTGCTT
TACTTGTCGCAAGTGCCATAGTTATCCACTTTAAATCTAATTTTACCAACCTTCTTATACTGTCA
CAGATTACACAATATTGTAGACATCGCCCTAAACCTAAAAAAGTAAATACTTCCCCCTCTACCT
CTCTTGCTTATTACGCAGACGATTAACTGAATTTAAAATTACCCTTCTACCGTTGCCATGGGGCT
AGCTGCTATATAGCTATGAAGATCAAATCCCGGTTTTCATTGTAAATTTAAAAATATATAAGAAA
TAATCTGAAGCCGACTTTATTTTTACCCAACTACGAATCACTCATTTAAATTAAATAGGTTTATT
ATGCAAAATAATAAAGCTTGAATATATTCCTGTAATATAAGGTTAAATAAGTTATATTTCTATTT
ATTGTTTAACAATAATAATTAAATCATAGTCTATTTGATTTCGTAATGAGTTTGGCATTTTCTGT
CATGCGATCGTGTAAGTTATTTTGTATATTGTGGTTTGGTTATCTTATTCAAAATAAATTATTAA
CAAGGAGATTTAATATGGATCC

FIGURE 15

ATGTCCAGTACAGGATATGCTCCATTTTATCTCCGTTTTATTCAGTTCCCAAGTAATGAAGTTTT
ACTCTATGAATACTGGAAACTTGTTCAGAATTTTGTACAAAAGGTTAGTAAAATAACGGTAAGAT
TAGCACAAATCGTTGGCATTCTCGGCGAAAAACTATTTGGAAATACCAAAGTACTTTTAATGAT
GGCATGCTGGATATTGTGGTTTGGTTATCTTATTCAAAA

FIGURE 16

```
ATGTCCGGTACAGAATATGCTCCATTTTATCTCCGTTTTATTCAGTTCCCAAGTAATGAA
GTTTTACTCTATGAATACTGGAAACTTGTTCAGAATTTTGTACAAAAGGTTAGTAAAATA
ACGGTAAGATTAGCACAAATCGTTGGCATTCTCGGCGAAAAAACTATTTGGAAATACCAA
AGTACTTTTAATGATGGCATGCTGGAAGGTGAAGCAGCTAAACAAGAAGTTTCCCGCACT
TTAAGAAGTAGTGCTTTACTTGTCGCAAGTGCCATAGTTATCCACTTTAAATCTAATTTT
ACCAACCTTCTTATACTGTCACAGATTACACAATATTGTAGACATCGCCCTAAACCTAAA
AAAAGTAAATACTTCCCCCTCTACCTCTCTTGCTTATTACGCAGACGATTAACTGAATTT
AAAATTACCCTTCTACCGTTGCCATGGGGC
```

FIGURE 17

| M | S | S | T | G | Y | A | P | F | Y | L | R | F | I | Q | F |
|---|---|---|---|---|---|---|---|---|---|---|---|---|---|---|---|
| P | S | N | E | V | L | L | Y | E | Y | W | K | L | V | Q | N |
| F | V | Q | K | V | S | K | I | T | V | R | L | A | Q | I | V |
| G | I | L | G | E | K | T | I | W | K | Y | Q | S | T | F | N |
| D | G | M | L | D | I | V | V | W | L | S | W | S | K |   |   |

FIGURE 18

| M | S | G | T | E | Y | A | P | F | Y | L | R | F | I | Q | F |
|---|---|---|---|---|---|---|---|---|---|---|---|---|---|---|---|
| P | S | N | E | V | L | L | Y | E | Y | W | K | L | V | Q | N |
| F | V | Q | L | V | S | K | I | T | V | R | L | A | Q | I | V |
| G | I | L | G | E | K | T | I | W | K | Y | Q | S | T | F | N |
| D | G | M | L | E | G | E | A | A | K | Q | E | V | S | R | T |
| L | R | S | S | A | L | L | V | A | S | A | I | V | I | H | F |
| K | S | N | F | T | N | L | L | I | L | S | Q | I | T | Q | Y |
| C | R | H | R | P | K | P | K | K | S | K | Y | F | P | L | Y |
| L | S | C | L | L | R | R | R | L | T | E | F | K | I | T | L |
| L | P | L | P | W | G |   |   |   |   |   |   |   |   |   |   |

COMPOSITION AND METHODS FOR DIAGNOSIS OF DISEASES ASSOCIATED WITH *ACTINOBACILLUS ACTINOMYCETEMCOMITANS* INFECTION

CROSS REFERENCE TO RELATED APPLICATIONS

This application is a continuation of U.S. application Ser. No. 08/374,843, filed on Jan. 18, 1995 now U.S. Pat. No. 5,726,016.

GOVERNMENT SUPPORT

Some portions of this invention have been made with U.S. Government support (Grant Nos. DE 10729 and DE 07118) from the National Institutes of Health and the U.S. Government may have certain rights in the invention.

FIELD OF THE INVENTION

The invention is directed to *Actinobacillus actinomycetemcomitans* induced disease.

BACKGROUND OF THE INVENTION

*Actinobacillus actinomycetemcomitans* (*A.a.*) is a nonenteric gram negative bacterium which is associated with a variety of infectious disease processes including endocarditis, subcutaneous abscesses, and several forms of periodontal disease (Block et al., 1973, A, J, Med. Sci. 276:387–392; Page et al., 1966, N. Engl. J. Med. 275:181–188; Zambon, 1985, J. Clin. Periodontal. 12:1–20; Zambon et al., 1983, Infect. Immun. 41:19–27). Juvenile periodontitis is an oral disease which afflicts adolescents and pre-teens and is caused by *A.a.* Symptoms include inflammation of the gingiva and destruction of the tissues supporting the teeth.

*A.a.* produces a variety of potential virulence factors including a proteinaceous leukotoxin (Kraig et al., 1990, Infect. Immun. 58:920–929; Lally et al., 1991, Microb. Pathog. 111–121) which is a member of the RTX (repeats-in-toxin) family of bacterial cytolysins (Welch, 1991, Mol. Microbiol.5:521–528). *A.a.* leukotoxin exhibits a unique cytolytic specificity in that it destroys human polymorphonuclear leukocytes and macrophages, but does not lyse other types of cells, for example, epithelial and endothelial cells, fibroblasts, erythrocytes and platelets (Baehni et al., 1981, Arch. Oral Biol. 27:671–676; Taichman et al., 1980, Infect. Immun. 28:258–278; Taichman et al., 1984, J. Period. Res. 19:133–145; Taichman et al., 1987, Oral Microbiol. Immun. 2:97–104).

The *A.a.* leukotoxin is expressed from an operon comprising four genes designated 1txC, 1txA, 1txB, and 1txD. The structural gene encoding the *A.a* leukotoxin (1txA), encodes a 116 kDa peptide which is approximately 40 and 50% identical to the *Escherichia coli* alpha-hemolysin and *Pasteurella haemolytica* leukotoxin (Kraig et al., 1990, Infect. Immun. 58:920–929; Lally et al., 1989, Biochem. Biophys. Res. Commun. 159:256–272). The structure of the actual *A.a.* leukotoxin is similar to other RTX toxins based upon DNA sequence homology and on similarities in the mechanism of action of this class of toxins (Felmlee et al., 1985, J. Bacteriol. 163:94–105; Felmlee et al., 1988, Proc. Natl. Acad. Sci. USA 85:5279–5273; Ludwig et al., 1988, Mol. Gen. Genet. 214:553–561; Ludwig et al., 1987, Mol. Gen. Genet. 206:238–245). However, the *A.a.* leukotoxin differs from other RTX toxins in that it is not secreted from the bacterial cell (Lally et al., 1991, Microb. Pathog. 11:111–121). The products of the three remaining 1x genes, 1txB, 1txC and 1txD, are believed to be required for activation and transport of the leukotoxin in the cell.

At least two mRNAs are transcribed from the 1txCABD gene cluster (Spitznagel et al., 1991, Infect. Immun. 59:1394–1401). A predominant mRNA of 3.8 kb encodes 1txC and 1txA, and a less abundant mRNA of 8 kb encoding 1txCABD results when transcription fails to terminate at a rho-independent transcriptional terminator situated between 1txA and 1txB (Lally et al., Microb. Pathog. 11:111–121; Spitznagel et al., 1991, Infect. Immun. 59:1394–1401). Expression of leukotoxin varies among different strains of *A.a.* Analysis of several nonleukotoxic strains has revealed that they possess the 1tx operon but express only low steady state levels of 1tx mRNA relative to the highly leukotoxic strain, JP2 (Spitznagel et al., 1991, Infect. Immun. 59:1394–1401). The basis for this difference was unknown prior to the instant invention.

Thus, it is known that two populations of *A.a.* exist in the oral cavity, one producing high levels of leukotoxin and another producing low levels of leukotoxin. An understanding of the molecular basis for the difference between these two populations has provided a means for which there has been a long felt need, of differentiating between the two populations in order that appropriate treatment may be administered to a patient infected with a leukotoxic strain of *A.a.*, which patient may or may not have progressed to severe periodontal disease.

SUMMARY OF THE INVENTION

In one aspect, the invention features a primer comprising an oligonucleotide complementary to nucleotides +5 to −15 of the leukotoxin promoter in a JP2-like strain of *Actinobacillus actinomycetemcomitans*. In one embodiment of the invention, the strain of *Actinobacillus actinomycetemcomitans* is JP2.

In another aspect, the invention features a primer comprising an oligonucleotide complementary to nucleotides −471 to −487 of the leukotoxin promoter in a JP2-like strain of *Actinobacillus actinomycetemcomitans*. In one embodiment of this aspect of the invention, the strain of *Actinobacillus actinomycetemcomitans* is JP2.

Preferably, the primer comprises about 8–80 nucleotides. More preferably, the primer comprises about 10–50 nucleotides. Even more preferably, the primer comprises about 15–25 nucleotides. Yet more preferably, the primer comprises the sequence 5'-AACCTGATAACAGTATT [SEQ ID NO:1] -3'or the sequence 5'-TCCATATTAAATCTCCTTGT [SEQ ID NO: 2] -3.

The invention also features a primer comprising an oligonucleotide complementary to the JP2/652 breakpoint region of a leukotoxin promoter of a highly toxic strain of *Actinobacillus actinomycetemcomitans*, preferably, *Actinobacillus actinomycetemcomitans* strain JP2.

In one embodiment, the primer comprises a 3' region comprising no more than 5 nucleotides situated upstream and immediately adjacent to the breakpoint, the first of the 5 nucleotides of the 3' region (reading in the 5' to 3' direction) being complementary to the first nucleotide on the 5' side of the breakpoint. The primer further comprises a 5' region comprising about 8 to 80 nucleotides complementary to about 8 to 80 nucleotides downstream and immediately adjacent to the breakpoint, the first of the about 8 to 80 nucleotides of the 5' region (reading in the 3' to 5' direction) being complementary to the first nucleotide on the 3' side of the breakpoint.

In yet another embodiment, the primer comprises a 3' region comprising 1 to 4 nucleotides situated upstream and immediately adjacent to the breakpoint, the first of the 1 to 4 nucleotides of the 3' region (reading in the 5' to 3' direction) being complementary to the first nucleotide on the 5' side of the breakpoint. The primer further comprises a 5' region comprising about 8 to 80 nucleotides complementary to about 8 to 80 nucleotides downstream and immediately adjacent to the breakpoint, the first of the about 8 to 80 nucleotides of the 5' region (reading in the 3' to 5' direction) being complementary to the first nucleotide on the 3' side of the breakpoint.

In yet another embodiment, the primer comprises a 3' region comprising 1 to 4 nucleotides situated upstream and immediately adjacent to the breakpoint, the first of the 1 to 4 nucleotides of the 3' region (reading in the 5' to 3' direction) being complementary to the first nucleotide on the 5' side of the breakpoint. The primer further comprises a 5' region comprising about 10 to 50 nucleotides complementary to about 10 to 50 nucleotides downstream and immediately adjacent to the breakpoint, the first of the about 10 to 50 nucleotides of the 5' region (reading in the 3' to 5' direction) being complementary to the first nucleotide on the 3' side of the breakpoint.

In another embodiment, the primer comprises a 3' region comprising 1 to 4 nucleotides situated upstream and immediately adjacent to the breakpoint, the first of the 1 to 4 nucleotides of the 3' region (reading in the 5' to 3' direction) being complementary to the first nucleotide on the 5' side of the breakpoint. The primer further comprises a 5' region comprising about 15 to 25 nucleotides complementary to about 15 to 25 nucleotides downstream and immediately adjacent to the breakpoint, the first of the about 15 to 25 nucleotides of the 5' region (reading in the 3' to 5' direction) being complementary to the first nucleotide on the 3' side of the breakpoint.

Most preferably, the primer of the invention being complementary to the breakpoint region is selected from the group consisting of ov1 and ov4.

The invention further features a method of determining the presence or absence of a highly toxic or non-toxic strain of *Actinobacillus actinomycetemcomitans* in a human patient. The method involves performing a polymerase chain reaction on DNA in a sample obtained from a patient using a primer comprising an oligonucleotide complementary to nucleotides +5 to −15 of the *Actinobacillus actinomycetemcomitans* JP2 leukotoxin promoter and a primer comprising an oligonucleotide complementary to nucleotides −471 to −487 of the *Actinobacillus actinomycetemcomitans* JP2 leukotoxin promoter. The presence of a 492 bp DNA fragment in the polymerase chain reaction is indicative of the presence of a highly toxic strain in the sample and the absence of a 492 bp DNA fragment is indicative of the absence of a highly toxic strain in the sample. Further, the presence of a 1022 bp DNA fragment in the polymerase chain reaction is indicative of the presence of a non-toxic strain in a sample and the absence of a 1022 bp DNA fragment is indicative of the absence of a non-toxic strain in the sample.

The invention also features a method of determining the presence or absence of a highly toxic strain of *Actinobacillus actinomycetemcomitans* in a human patient. The method involves performing a polymerase chain reaction on DNA in a sample obtained from the patient using a primer comprising an oligonucleotide complementary to the *Actinobacillus actinomycetemcomitans* JP2/652 leukotoxin promoter breakpoint region and a primer comprising an oligonucleotide complementary to nucleotides −471 to −487 of the *Actinobacillus actinomycetemcomitans* JP2 promoter. The presence of a 492 bp amplification product is indicative of the presence of a highly toxic strain in the sample and the absence of a 492 bp amplification product is indicative of the absence of a highly toxic strain in the sample.

Also featured in the invention is an isolated DNA sequence substantially homologous to a DNA sequence specifying an *Actinobacillus actinomycetemcomitans* strain 652 leukotoxin promoter. Preferably, the DNA sequence is that shown in FIG. 6.

The invention further features an isolated DNA sequence comprising an *Actinobacillus actinomycetemcomitans* strain JP2/652 leukotoxin promoter breakpoint region. Preferably, this DNA sequence comprises at least 4 nucleotides substantially homologous to *Actinobacillus actinomycetemcomitans*JP2 breakpoint region.

In yet another aspect, the invention features a method of determining the presence or absence of a highly toxic strain of *Actinobacillus actinomycetemcomitans* in a human patient. This method involves isolating DNA from a sample obtained from the patient, digesting the DNA with at least one restriction enzyme, and hybridizing to the DNA a probe capable of distinguishing between the leukotoxin promoter sequence of a highly toxic strain of *Actinobacillus actinomycetemcomitans* and the leukotoxin promoter sequence of a nontoxic strain of *Actinobacillus actinomycetemcomitans*.

In yet another aspect of the invention there is provided a kit comprising a primer comprising an oligonucleotide complementary to nucleotides +5 to −15 of the *Actinobacillus actinomycetemcomitans* JP2 leukotoxin promoter, a primer comprising an oligonucleotide complementary to nucleotides −471 to −487 of the *Actinobacillus actinomycetemcomitans* JP2 leukotoxin promoter, *Actinobacillus actinomycetemcomitans* strain JP2 and strain 652 DNA, and instructions for using the kit.

Also featured in the invention is a kit comprising a primer comprising an oligonucleotide complementary to the *Actinobacillus actinomycetemcomitans* JP2/652 leukotoxin promoter breakpoint region, a primer comprising an oligonucleotide complementary to nucleotides −471 to −487 of the *Actinobacillus actinomycetemcomitans* JP2 promoter, *Actinobacillus actinomycetemcomitans* strain JP2 and strain 652 DNA, and instructions for using the kit.

In another aspect, there is provided a kit comprising a probe capable of distinguishing between the leukotoxin promoter sequence of a highly toxic strain of *Actinobacillus actinomycetemcomitans* and the leukotoxin promoter sequence of a nontoxic strain of *Actinobacillus actinomycetemcomi* tans, *Actinobacillus actinomycetemcomitans* strain JP2 and strain 652 DNA, and instructions for using the kit.

The invention further features an isolated DNA sequence substantially homologous to the DNA sequence encoding the *Actinobacillus actinomycetemcomitans* strain JP2 ORF. Preferably, the DNA sequence is 5'
-ATGTCCAGTACAGGATATGCTCCATTTTATCTCCG TTTTATTCAGTTCCCAAGTAATGAA GTTTTACTC- TATGAATACTGGAAACTTGTTCA- GAATTTTGTACAAAAGGTTAGTAAAATA ACGG- TAAGATTAGCACAAATCGTTGGCATTCTCGGCG AAAAAACTATTTGGAAATACCAA AGTACTTT- TAATGATGGCATGCTGGATATTGTG- GTTTGGTTATCTTATTCAAAA [SEQ ID NO: 3] -3'.

Also featured is an isolated DNA sequence substantially homologous to the DNA sequence encoding the *Actinoba-*

*cillus actinomycetemcomitans* strain 652 ORF. Preferably, this DNA sequence is 5'
-ATGTCCGGTACAGAATATGCTCCATTTTATCTCCG-
TTTTATTCAGTTCCCAAGTAATGAA GTTTTACTC-
TATGAATACTGGAAACTTGTTCA-
GAATTTTGTACAAAAGGTTAGTAAAATA ACGG-
TAAGATTAGCACAAATCGTTGGCATTCTCGGCG
AAAAAACTATTTGGAAATACCAA AGTACTTT-
TAATGATGGCATGCTGGAAGGTGAAG-
CAGCTAAACAAGAAGTTTCCCGCACT TTAA-
GAAGTAGTGCTTTACTTGTCGCAAGTGCCATAG
TTATCCACTTTAAATCTAATTTT ACCAACCTTCT-
TATACTGTCACAGATTACACAATATTG-
TAGACATCGCCCTAAACCTAAA AAAAG-
TAAATACTTCCCCCTCTACCTCTCTTGCTTATTAC
GCAGACGATTAACTGAATTT AAAATTACCCTTC-
TACCGTTGCCATGGGGC [SEQ ID NO:4] -3'.

In another aspect of the invention, there is provided an isolated amino acid sequence substantially homologous to *Actinobacillus actinomycetemcomitans* strain JP2 ORF and an isolated amino acid sequence substantially homologous to *Actinobacillus actinomycetemcomitans* strain 652 ORF. The amino acid sequence of *Actinobacillus actinomycetemcomitans* strain JP2 ORF is as follows, reading from the amino terminus to the carboxyl terminus of the molecule: MSSTGYAPFYLRFIQFPSNEVLLYEY-WKLVQNFVQKVSKITVRLAQIVGILGEKTIWKYQ STFNDGMLDIVVWLSYSK[SEQ ID NO: 5].

The amino acid sequence of *Actinobacillus actinomycetemcomitans* strain 652 ORF is as follows, reading from the amino terminus to the carboxyl terminus of the molecule: MSGTEYAPFYLRFIQFPSNEVLLYEY-WKLVQNFVQKVSKITVRLAQIVGILGEKTIWKYQ STFNDGMLEGEAAKQEVSRTLRSSAL-LVASAIVIHFKSNFTNLLILSQITQYCRHRPKPK KSKYFPLYLSCLLRRRLTEFKITLLPLPWG [DEQ ID NO:6].

As used herein, the term "non-toxic" means minimally toxic. This term is associated herein with 652-like strains of *A.a.* which contain the 1tx operon and therefore express a low level of leukotoxin. The terms "toxic" or "highly toxic" strains of *A.a.* refer to JP2-like strains which express high levels of leukotoxin.

Complementary as used herein also refers to the subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs).

As used herein, the term homologous refers to the subunit sequence similarity between two polymeric molecules e.g., between two nucleic acid molecules, e.g., between two DNA molecules. When a subunit position in both of the two molecules is occupied by the same monomeric subunit, e.g., if a position in each of two nucleic acid molecules is occupied by adenine, then they are homologous at that position. The homology between two sequences is a direct function of the number of matching or homologous positions, e.g., if half (e.g., 5 positions in a polymer 10 subunits in length) of the positions in two nucleic acid sequences are homologous then the two sequences are 50% homologous; if 70% of the positions, e.g., 7 out of 10, are matched or homologous, the two sequences share 70% homology. By way of example, the nucleic acid sequences GAATTC and GAAGGT share 50% homology.

As used herein, the term homologous as it refers to an amino acid sequence refers to the subunit sequence similarity between two peptide molecules. When a subunit position in both of the two molecules is occupied by the same monomeric subunit, e.g., if a position in each of two peptide molecules is occupied by alanine, then they are homologous at that position. The homology between two sequences is a direct function of the number of matching or homologous positions, e.g., if half (e.g., 5 positions in a polymer 10 subunits in length) of the positions in two nucleic acid sequences are homologous then the two sequences are 50% homologous; if 70% of the positions, e.g., 7 out of 10, are matched or homologous, the two sequences share 70% homology. By way of example, the amino acid sequences ala-phe-tyr-gly-val-ser and ala-phe-tyr-glu-cys-gln share 50% homology.

By substantially homologous, as used herein referring to a nucleic acid sequence, is meant DNA sequence which shares at least 60% homology with a known, named DNA sequence. Preferably, the DNA sequence is 70% homologous, more preferably, it is 80% homologous and most preferably, it is at least 90% homologous with the known, named DNA sequence.

By substantially homologous, as used herein referring to an amino acid sequence, is meant an amino acid sequence which shares at least 60% homology with a known, named amino acid sequence. Preferably, the amino acid sequence is 70% homologous, more preferably, it is 80% homologous and most preferably, it is at least 90% homologous with the known, named amino acid sequence.

Further, as used herein, by an isolated DNA is meant a DNA which is separated from components which naturally accompany it, including the sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA, or lipid which naturally accompany it in the cell.

Further, as used herein, by an isolated amino acid sequence is meant a peptide which is separated from components which naturally accompany it, including the sequences which flank it in a naturally occurring state, e.g., a peptide fragment which has been removed from the sequences which are normally adjacent to the fragment. The term also applies to peptides which have been substantially purified from other components which naturally accompany the peptide, e.g., RNA or DNA, or lipid which naturally accompany it in the cell.

By the term JP2/652 breakpoint region, as used herein, is meant that point on the leukotoxin promoter sequence of toxic *A.a.* strains at which the unique 530 bp region of non-toxic *A.a.* resides (between nucleotides −54 and −55 in FIG. 1A). Hence, the breakpoint is represented by the sequence GXA, where X is no nucleotide in highly toxic strains of *A.a.* and is 530 nucleotides in non-toxic strains of *A.a.,* which 530 nucleotides are substantially homologous to the unique 530 bp region of *A.a.* strain 652. The breakpoint region is understood to include the sequence GXA and at least one additional nucleotide on each of the 5' and 3' sides of this sequence, each additional nucleotide being substantially homologous to identically positioned nucleotides in the JP2 breakpoint region. Preferably, the region includes the sequence GXA and between 2 to 5 additional nucleotides on each of the 5' and 3' sides of this sequence, each additional nucleotide being substantially homologous to identically positioned nucleotides in the JP2 breakpoint region. The region may include the sequence GXA and 6 or more additional nucleotides on each of the 5' and 3' sides of this sequence, each additional nucleotide being substantially homologous to identically positioned nucleotides in the JP2 breakpoint region.

BRIEF DESCRIPTION OF THE DRAWINGS

FIG. 1A is the nucleotide sequence of the promoter region FIG. 1B is [SEQ ID NO:2] and a diagram of the genetic organization of the A.a.

JP2 1tx operon. The sequence shown begins at the termination codon of the A.a. glyA gene and ends at nucleotide 5 of 1txC. Opposing arrows over the sequence are inverted repeats and asterisks indicate mismatched positions. The −10 and −35 regions of the two 1tx promoters ($P_1$ and $P_2$) are labelled, and the sites of initiation of transcription predicted by primer extension are indicated by vertical arrows. The deduced amino acid sequence of the upstream ORF is indicated in boldface type[SEQ ID NO:8]. RBS denotes ribosome binding sequences and T represents the transcriptional termination sequence between 1txAB. The nucleotide sequence is numbered on the right with +1 being the adenine residue of the 1txC initiation codon. The deduced peptide sequence is numbered on the left.

Figure 2:
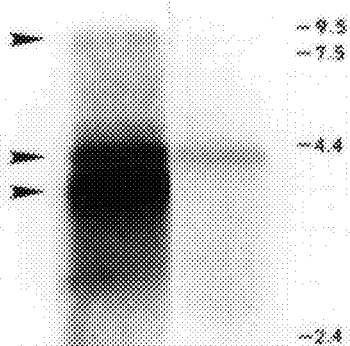

FIG. 2 is a photograph of a gel depicting Northern hybridization analysis of A.a. JP2 RNA using probes specific for 1txA (lane 1) and the region encompassing the ORF (lane 2). The three mRNAs transcribed from the 1tx operon indicated by the arrowheads on the left have the following sizes: 8 kb, 4.2 kb and 3.8 kb. The relative positions of standard size RNAs are indicated to the right of the gel.

Figure 3A:
Figure 3B:

FIG. 3 comprising panels A and B is a photograph of two gels depicting primer extension analysis of A.a. RNA. The 340 and 40 base extension products (lanes P) are shown in panels A and B, respectively. Sequencing reactions from the same primer used in the primer extensions are shown and labeled in each panel. This sequence is therefore the complement of that shown in FIG. 1A. FIG. 3A Sequence complementary to nucleotides −301 to −382 in FIG. 1A; FIG. 3B Sequence complementary to nucleotides −28 to −52 in FIG. 1A. Initiation of transcription is predicted to occur at nucleotides −38 and −335.

Figure 4A:
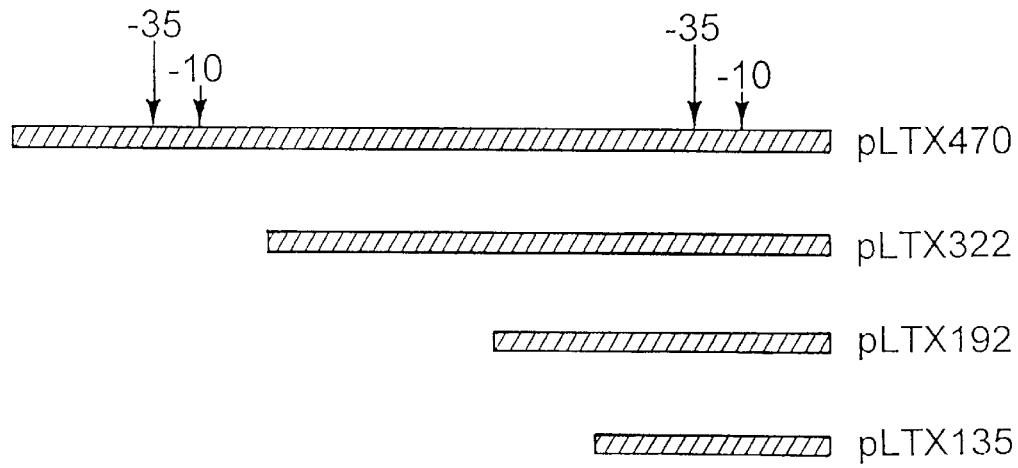

FIG. 4 comprising FIGS. A and B are diagrams depicting analysis of the JP2 1tx promoter 1acZ fusion plasmids. FIG. 4A is a schematic representation of the intact 470 bp 1tx promoter (p1tx470) and the deletion constructs containing 322, 192, 135 and 63 bp as indicated.

Figure 1B:
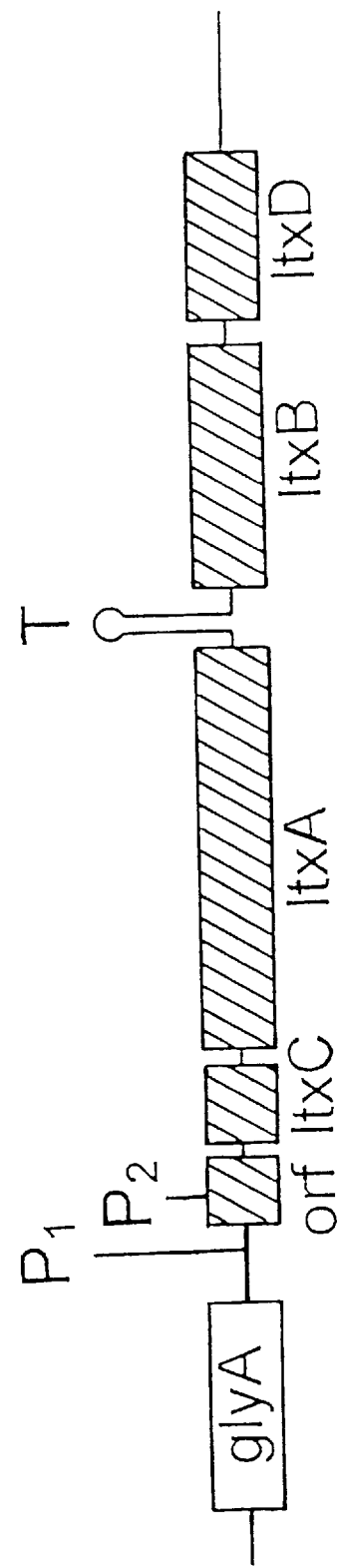
Figure 4B:
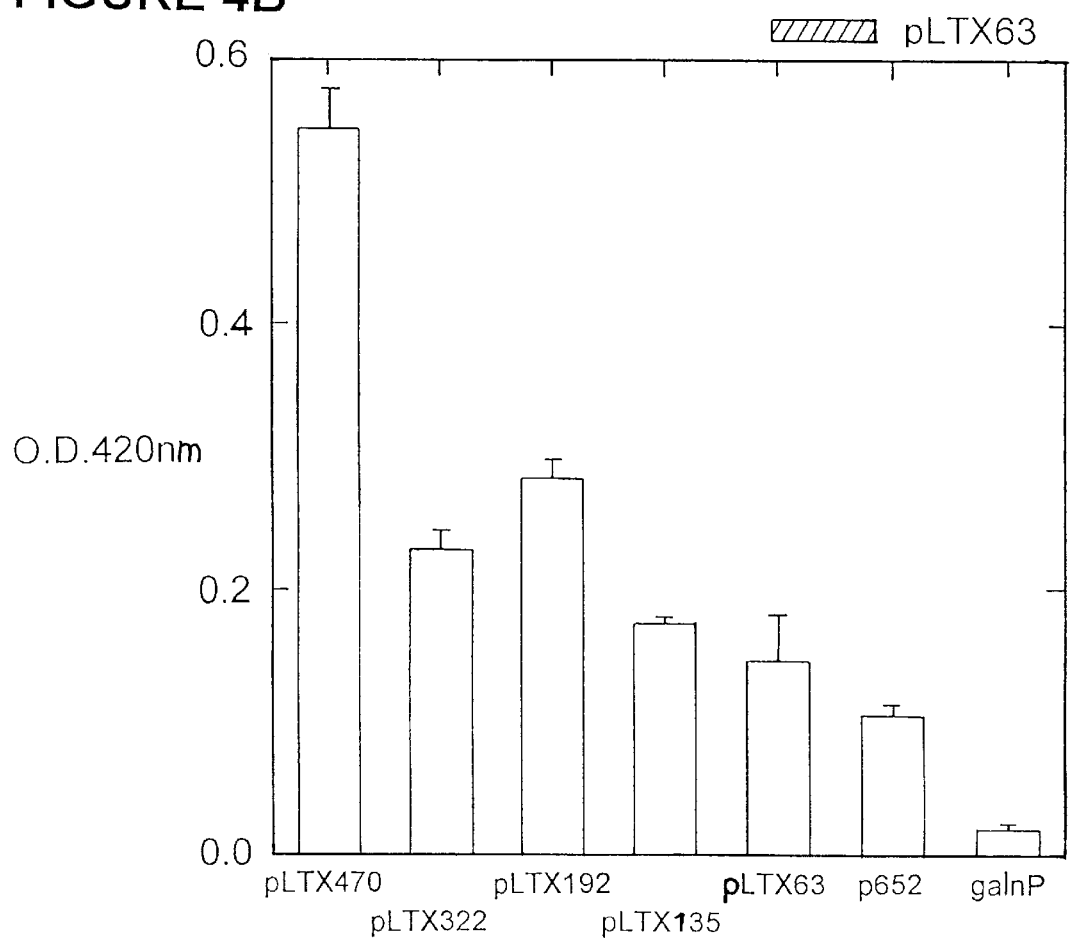

The 3' ends of all of the promoter constructs terminate at the translation start codon of 1txC. The relative positions of the JP2 −10 and −35 elements identified in FIG. 1A are shown on p1tx470. FIG. 4B is a graph showing relative levels β-galactosidase activity expressed by the 1acZ fusion constructs. β-Galactosidase activity was determined by measuring the increase in $OD_{420}$ upon cleavage of the calorimetric substrate ONPG. Construct p652 contains the intact 1,000 bp promoter fragment from strain 652 and ga1np contains a promoterless 1acZ gene. The levels of β-galactosidase activity shown for p652 and ga1nP were obtained using 10-fold more cell extract than did the JP2 deletion constructs.

Figure 5:
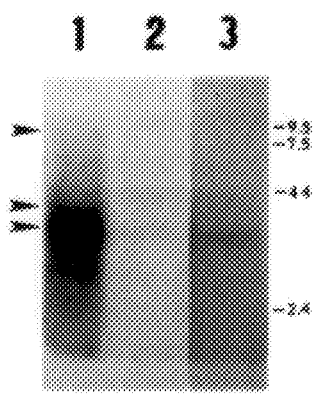

FIG. 5 is a photograph of a gel depicting a comparison of the steady state levels of 1tx mRNA expressed by A.a. JP2 (lane 1) and 652 (lanes 2 and 3). Blots were hybridized with a probe encoding 1txA. Lanes 1 and 2 were exposed to X ray film for 1 hour and lane 3 was exposed for 18 hours.

FIG. 6 depicts the nucleotide sequence of A.a. strain 652 1tx promoter region [SEQ ID NO:9]. The portion of the sequence shown in boldface type and double underlined represents the region which is absent in the 1tx promoter of strain JP2. For comparative purposes, the −10 and −35 elements that are analogous to those found in the JP2 promoter are indicated. The promoter elements used by strain 652 have not been determined. The deduced amino acid sequence of the upstream ORF is also shown [SEQ ID NO:10]; the amino acid numbers are indicated on the left. The nucleotide sequence is numbered on the right with +1 representing the adenine of the 1tx start codon.

Figure 7:

FIG. 7 is a photograph of a typical Southern blot hybridization analysis using restriction fragment length polymorphism (RFLP) of the promoter sequences from the 1tx promoters of A.a. strains JP2 and 652. This Figure depicts detection of A.a. EcoRI RFLP using a probe derived from the leukotoxin promoter. EcoRI digested genomic DNA obtained from A.a. strains JP2 (lane 1) and 652 (lane 2) was electrophoresed through 0.8% agarose and transferred to a nitrocellulose filter. The filter was hybridized to a 492 bp probe corresponding to the 1tx promoter region of strain JP2. Fragments which hybridize to the probe (3.4 and 3.9 kb in size) are indicated by arrows.

Figure 8:
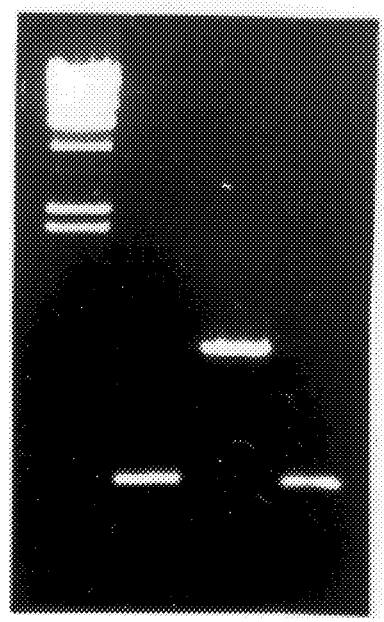

FIG. 8 is a photograph of a typical PCR amplification gel showing identification of the 1tx promoter region using PCR. Genomic DNA isolated from A.a. strains 363 (lane 2), 366 (lane 3), and 651 (lane 4) was analyzed by PCR using primers which anneal to nucleotides +5 to −15 and −471 to −487 of the JP2 promoter. The amplified products were analyzed by agarose gel electrophoresis and were compared with known DNA size markers (lane 1). A 492 bp DNA product was evident in the lanes containing DNA obtained from strains 363 and 651, which product is characteristic of strain JP2 and other highly toxic strains of A.a. In contrast a 1000 bp DNA fragment was evident in the lane containing DNA obtained from strain 366. This is characteristic of non-toxic strains of A.a.

FIG. 9 depicts a comparison of the DNA sequence of the leukotoxin promoter region of strains JP2 and 652 in the breakpoint region. The JP2 sequence shown [SEQ ID NO:11] corresponds to nucleotides −63 to −33 in FIG. 1A. The JP2 and 652 [SEQ ID NO:12] sequences shown are identical from nucleotides −33 to −54. The remainder of the 652 sequence represents the 3' end of the 530 bp domain which is absent in the JP2 promoter region. Thus, the sequence identity of the JP2 and 652 1tx promoters "breaks" at nucleotide −55. The sequences of the oligonucleotide primers designated as ov1 [SEQ ID NO:13] and ov4 [SEQ ID NO:14] are also shown. These oligonucleotides are complementary to the breakpoint region of the JP2 sequence but possess one and four nucleotides, respectively, at their 3' ends which are not complementary to the corresponding region of the 652 promoter sequence.

FIG. 10 comprising FIG. 10A and 10B, is a schematic diagram depicting annealing of ov1 and ov4 oligonucleotide primers complementary to the JP2 and 652 1tx promoter regions. The entire ov1 and ov4 sequences are complementary to the JP2 breakpoint region and form the duplexes shown in FIG. 10A. Since both primers span the breakpoint, the ov1 and ov4 sequences do not anneal to a contiguous region of the 652 promoter region and thus only form the imperfect duplexes shown in FIG. 10B in which the 3' ends of the oligonucleotide primers remain unannealed to the 652 promoter template.

Figure 11:
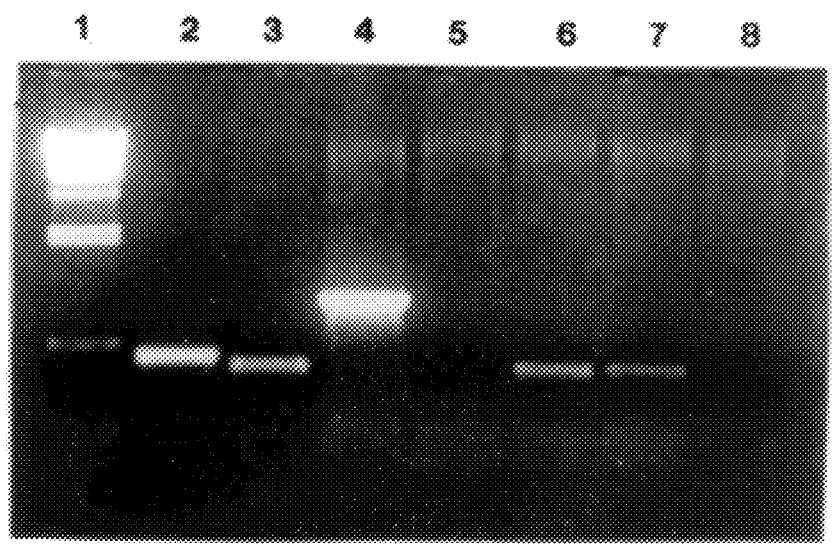

FIG. 11 is a photograph of a gel depicting the presence or absence of a 492 bp amplification product following PCR amplification of either 652 or JP2 genomic DNA or a combination of 652 and JP2 genomic DNA in the presence of various oligonucleotide primer sequences. Lane 1, DNA size markers; lane 2, JP2 DNA and control primers which anneal to nucleotides +5 to −15 and −471 to −487 of the JP2 promoter; lane 3, JP2 DNA, ov4 primer; lane 4, 652 DNA, control primers; lane 5, 652 DNA, ov4 primer; lane 6, a 1:10 ratio of JP2:652 DNA, ov4 primer; lane 7, a 1:100 ratio of JP2:652 DNA, ov4 primer; lane 8, a 1:1000 ratio of JP2:652 DNA, ov4 primer.

FIG. 12 is a graph depicting the effect of ORF9.2 expression on the growth of E.coli DH5α. The region of the JP2 promoter sequence encoding the open reading frame situated upstream of 1txc was amplified by PCR and inserted into plasmid pMMB67 (Furste et al., 1986, Gene 48:119–131) such that expression of pORF9.2 is under the control of the vector derived 1ac promoter. E.coli cells were transformed with the resulting plasmid and their growth was monitored at various times post-transformation by absorbance at 675 nm. Induction of ORF9.2 expression driven by the 1ac promoter was accomplished by the addition of IPTG to the cultures after two hours of growth at 37° C. The symbols used are as follows: Open circles —E.coli containing pMMB67, no induction; closed circles —E.coli containing pMMB67 induced with IPTG; open triangles —E.coli containing ORF9.2, no induction; closed triangles —E.coli containing ORF9.2, induced with IPTG.

FIG. 13 is the nucleotide sequence of A.a. strain JP2 leukotoxin promoter [SEQ ID NO:16].

FIG. 14 is the nucleotide sequence of A.a. strain 652 promoter.

FIG. 15 is the nucleotide sequence encoding A.a. strain JP2 ORF [SEQ ID NO:17].

FIG. 16 is the nucleotide sequence encoding A.a. strain 652 ORF [SEQ ID NO:18].

FIG. 17 is the amino acid sequence of A.a. strain JP2 ORF.

FIG. 18 is the amino acid sequence of A.a. strain 652 ORF.

DETAILED DESCRIPTION OF THE INVENTION

A diagnostic test has been developed which differentiates highly toxic strains of A.a. from non-toxic strains. The test is capable of identifying the presence of highly toxic A.a. strains in a background of 1000-fold excess of non-toxic A.a. strains. The test is useful for identifying patients susceptible to periodontitis; it is useful for determining the extent and/or progression of periodontal disease in an individual; and, the test is useful for identifying sites in the mouth which harbor high levels of leukotoxic A.a. and which may be susceptible to tissue breakdown, a known characteristic of periodontitis. The test is further useful for identifying highly toxic strains of A.a. in other tissues of a patient suspected of having endocarditis, subcutaneous abscess, meningitis or osteomyelitis. Further, the test may also be useful for detecting the presence of highly toxic strains of A.a. associated as a secondary organism in mycoses (fungal infections).

It has been discovered that there are significant differences in the promoter region which drives transcription of the leukotoxin operon between highly toxic and non-toxic strains of A.a. The leukotoxin promoter in the genome of non-toxic strains possesses a domain of 530 base pairs which is absent in the leukotoxin promoter in the genome of toxic organisms. The absence of this domain results in the positioning of an upstream promoter, which normally controls expression of a gene unrelated to the leukotoxin gene, into close proximity with the leukotoxin promoter. As a consequence, expression of the leukotoxin operon of a highly toxic strain of A.a. is driven by two promoters, while expression of the operon of a non-toxic strain is driven by only one promoter. This difference forms the basis of the diagnostic test of the invention in that it is possible using either RFLP or PCR analysis to differentiate between highly toxic and non-toxic strains of A.a.

Highly toxic strains of A.a., exemplified herein by strain JP2, contain a DNA sequence within the promoter region of the leukotoxin operon which is highly conserved. Among four highly toxic strains examined, only one base change was identified within the 470 base pair promoter sequence. Similarly, the leukotoxin operon promoter region of non-toxic strains of A.a., exemplified herein by strain 652, is also highly conserved. Again, among three non-toxic strains examined, only a three base changes in one thousand bases was identified. Guthmiller et al. (Microbial. Pathog. 14:103–115, 1993) have also demonstrated conservative sequences within the leukotoxin gene among various toxic and non-toxic strains of A.a. In fact other studies also suggest, contrary to the present invention, that leukotoxin promoter sequences in highly toxic and non-toxic strains are conserved among each other, in that very little sequence diversity between toxic and non-toxic strains was observed in the leukotoxin A region of the genome as assessed by RFLP (Goncharoff et al., 1993, Oral Microbiol. Immunol. 8:105–110; Tonjum et al., 1993, J. Clinical Microbiol., 31:1856–1859; Lin et al., 1994, J. Formos Med. Assoc. 93:289–293). Thus, until the present invention, there was no indication in the art that highly toxic strains could be distinguished from non-toxic strains on the basis of the leukotoxin promoter sequence.

As used herein, a toxic strain of A.a. is considered to be a JP2-like strain of A.a., while a non-toxic strain of A.a. is considered to be a 652-like strain of A.a. Thus, "JP2"and "652"as used herein, refer to specific strains of A.a. and/or, when these terms are used generally herein, they refer to toxic and non-toxic strains of A.a. with regard to leukotoxin production.

The nucleotide sequence of the highly toxic and non-toxic leukotoxin promoter regions of A.a. are given in FIGS. 13 and 14, respectively. According to the methods of the invention, the difference between the nucleotide sequences of these two promoter regions may be exploited to generate several tests which facilitate differentiation of highly toxic strains of A.a. from non-toxic strains of this bacterium.

The test of the invention allows identification of individuals who harbor toxic A.a. and who therefore may be susceptible to disease. Thus, the test is useful for any individual needing such a test. To perform the test, a crude microbiological sample is obtained from the oral cavity of a patient using standard methods such as paper point sampling of the gingival crevice or curettage (scraping of dental plaque). Additional samples for testing are obtained as follows: for endocarditis, a blood sample is taken; for subcutaneous abscess, fluid (pus) is obtained from the abscess; for meningitis, spinal fluid is obtained; for osteomyelitis, a bone biopsy or fluid (pus) sample is obtained; and, in cases of mycoses, a tissue biopsy is obtained. Methods for obtaining the above-mentioned samples are well known to those skilled in the art.

In one of the methods of the invention, RFLP analysis, nucleic acid is isolated from a sample obtained from a patient suspected of being infected with a highly toxic strain of *A.a.* DNA so obtained is digested with a variety of restriction enzymes and the resulting fragments are separated by gel electrophoresis, transferred to a solid support and hybridized to a probe which is capable of distinguishing between the leukotoxin promoter sequence of *A.a.* strain JP2 and *A.a.* strain 652. Methods for isolation of DNA, restriction enzyme digestion and hybridization are well known in the art and are described in Sambrook et al. (1989, Molecular Cloning: A Laboratory Manual, Cold Spring Harbor, N.Y.). Restriction enzymes which are useful for digestion of *A.a.* DNA include any known restriction enzyme predicted to cleave the leukotoxin promoter region of either *A.a.* strain JP2 or strain 652. Preferably, the restriction enzymes are PstI, EcoRI, BamHI, HindIII, SmaI, SphI, SalI, BglII, NcoI and NdeI. More preferably, the restriction enzymes useful for digestion of *A.a.* DNA are PstI, EcoRI, BamHI and HindIII.

Probes which are useful for distinguishing between highly toxic strains and non-toxic strains of *A.a.* by RFLP analysis are those sequences of DNA or RNA which hybridize specifically to both promoter sequences such that the size of the fragment which hybridizes to the probe is indicative of the presence or absence of either the JP2 or the 652 leukotoxin promoter sequences. Preferably, the probe comprises DNA complementary to the DNA sequence residing upstream of the 1txC gene and which hybridizes to the 1tx promoter region. More preferably, the probe comprises the region of DNA situated between the 1txC and glyA genes. Even more preferably, the probe comprises 492 nucleotides corresponding to the sequence shown in FIG. 1A. Prior to hybridization to restriction fragments, the probe is labelled with either a radioactive label or with a non-radioactive label, using techniques such as nick-translation, random primer labelling, PCR, or other techniques common in the art and described in Sambrook, Supra. Methods for detection of labelled probe hybridized to immobilized fragments of DNA are also well know in the art and are described in Sambrook, Supra.

In another method of the invention, tests based on PCR technology may be performed to identify highly toxic and non-toxic *A.a.* strains thereby distinguishing these strains from each other. In one such test, the entire 1tx promoter region is amplified from an unidentified sample of DNA isolated from a crude microbiological sample. The presence or absence of highly toxic strains in the test sample is determined by the presence of two specific amplification products of defined sizes. One of these products indicates the presence of the JP2-like promoter sequence in the sample and the other sequence indicates the presence of the 652-like promoter sequence in the sample. The presence of both fragments is an indication that both toxic and non-toxic strains of *A.a.* are present in the sample.

Primers which are useful for amplification of the JP2-like and 652-like promoter sequences comprise oligonucleotides complementary to nucleotides at about +5 to −15 and nucleotides at about −471 to −487 of the leukotoxin promoter in a highly toxic strain of *A.a.* One of the oligonucleotide primers must be capable of annealing to DNA sequences downstream of the JP2 breakpoint region while the other must be capable of annealing to DNA sequences upstream of the JP2 breakpoint region. Further, the products formed by amplification must be readily detectable by gel electrophoresis. Thus, useful oligonucleotide pairs, wherein one anneals downstream and the other anneals upstream of the breakpoint region (nucleotide −55), are those which anneal within the 1txC and glyA genes, respectively. Most preferably, the downstream oligonucleotide anneals to nucleotides at about +5 to −15 and the upstream oligonucleotide anneals to nucleotides at about −471 to −487 of the JP2 promoter sequence. Preferably, the primers comprise 8–80 nucleotides in length. More preferably, the primers comprise 10–50 nucleotides in length. Even more preferably, the primerscomprise 15–25 nucleotides in length. Most preferably, one of the primers comprises the sequence 5' -AACCTGATAACAGTATT -3' [SEQ ID NO:1] and the other primer comprises the sequence 5'- TCCATAT-TAAATCTCCTTGT -3' [SEQ ID NO:2]. When the latter two primers are used in the test of the invention, the products of PCR amplification are 492 bp and 1022 bp, respectively. If both highly toxic and minimally toxic strains are present in the same test sample, PCR amplification will result in the presence of both a 492 and a 1022 bp fragment.

In a second PCR based test capable of distinguishing between highly toxic and non-toxic strains of *A.a.*, the specificity of this test is derived from the design of the downstream oligonucleotide primer. This primer is designed to span the point on the JP2-like sequence at which the unique 530 bp region in *A.a.* strain 652 resides (between nucleotides −54 and −55 in FIG. 1A). This region has been designated the "breakpoint" region of the JP2 promoter sequence.

The upstream oligonucleotide primer used in this test is that described for the first test, i.e., a primer capable of hybridizing to about −487 to −471 in the JP2 promoter region. The downstream primer used in this test anneals to a region spanning the breakpoint. The 3' region of this primer comprises no more than 5 nucleotides situated upstream and immediately adjacent to the breakpoint, the first of the 5 nucleotides of the 3' region (reading in the 5' to 3' direction) being complementary to the first nucleotide on the 5' side of the breakpoint. The 5' region of the primer comprises about 8 to 80 nucleotides which are complementary to about 8 to 80 nucleotides downstream and immediately adjacent to the breakpoint, the first of the about 8 to 80 nucleotides of the 5' region (reading in the 3' to 5' direction) being complementary to the first nucleotide on the 3' side of the breakpoint.

Preferably, the 3' region of the downstream primer comprises no more than 1 to 4 nucleotides situated upstream and immediately adjacent to the breakpoint, the first of the 1 to 4 nucleotides of the 3' region (reading in the 5' to 3' direction) being complementary to the first nucleotide on the 5' side of the breakpoint. The 5' region of the primer comprises about 8 to 80 nucleotides which are complementary to about 8 to 80 nucleotides downstream and immediately adjacent to the breakpoint, the first of the about 8 to 80 nucleotides of the 5' region (reading in the 3' to 5' direction) being complementary to the first nucleotide on the 3' side of the breakpoint.

More preferably, the 3' region of the downstream primer comprises 1 to 4 nucleotides situated upstream and immediately adjacent to the breakpoint, the first of the 1 to 4 nucleotides of the 3' region (reading in the 5' to 3' direction) being complementary to the first nucleotide on the 5' side of the breakpoint. The 5' region of the primer comprises about 10 to 50 nucleotides which are complementary to about 10 to 50 nucleotides downstream and immediately adjacent to the breakpoint, the first of the about 10 to 50 nucleotides of the 5' region (reading in the 3' to 5' direction) being complementary to the first nucleotide on the 3' side of the breakpoint.

is Yet more preferably, the 3' region of the downstream primer comprises 1 to 4 nucleotides situated upstream and immediately adjacent to the breakpoint, the first of the 1 to 4 nucleotides of the 3' region (reading in the 5' to 3' direction) being complementary to the first nucleotide on the 5' side of the breakpoint. The 5' region of the primer comprises about 15 to 25 nucleotides which are complementary to about 15 to 25 nucleotides downstream and immediately adjacent to the breakpoint, the first of the about 15 to 25 nucleotides of the 5' region (reading in the 3' to 5' direction) being complementary to the first nucleotide on the 3' side of the breakpoint.

More preferably, downstream primers useful in the second PCR test of the invention include primers designated as ov1 and ov4 the sequences of which are shown in FIG. 9.

The annealing conditions for the second PCR test are chosen to prevent the formation of a stable "loop-out" structure between the downstream primer and the 652 promoter sequence. This is accomplished by controlling the temperature of the annealing reaction.

There will now be described experiments, the results of which delineate the differences between the promoter regions of highly toxic and non-toxic strains of A.a., which difference forms the basis of the diagnostic tests of the invention.

Bacterial Strains.

A.a. strains used in this study are listed in Table 1. These strains were obtained from the bacterial collections of the individuals listed.

TABLE 1

Relationship of A. actinomycetemcomitans promoter structure and leukotoxicity

| Strain | Promoter class[a] | $10^6$ $LD_{50}$[b] | Source |
|---|---|---|---|
| JP2 | JP2 | 2.5 | N. Taichman |
| 652 | 652 | 50 | B. Shenker |
| Y4 | 652 | 50 | N. Taichman |
| NCTC 9710 | 652 | 25 | N. Taichman |
| ATCC 29523 | 652 | >50 | N. Taichman |
| ATCC 29524 | 652 | 25 | N. Taichman |
| 060192 | 652 | >50 | B. Shenker |
| HK890 | 652 | >50 | M. Kilian |
| HK905 | 652 | 25 | M. Kilian |
| HK910 | 652 | 25 | M. Kilian |
| HK968 | 652 | >50 | M. Kilian |
| HK969 | 652 | >50 | M. Kilian |
| HK970 | 652 | 25 | M. Kilian |
| HK971 | 652 | 50 | M. Kilian |
| HK973 | 652 | 50 | M. Kilian |
| HK909 | JP2 | 3 | M. Kilian |
| ER | JP2 | 3 | M. Kilian |

[a]Promoters were classified as 652-like or JP2-like on the basis of results of PCR amplification of the promoter region as described in Materials and Methods. Strains which amplify a 492 bp fragment were classified as JP2-like; those which amplified a 1022 bp fragment were classified as 652-like.
[b]$LD_{50}$ is defined as the number of bacterial cells required to lyse 50% of 2 × $10^5$ HL60 cells in 1 hour at 37° C.

The strains listed above were grown in PYG medium (5 g of Bacto Peptone, 5 g of Trypticase peptone, 10 g of yeast extract, 10 g of glucose, 8 mg of $CaCl_2$ 8 mg of $MgSO_4$, 40 mg of $K_2HPO_4$, 40 mg of $KH_2PO_4$/400 mg of $NaHCO_1$3,and 80 mg of NaCl in 1 liter of distilled $H_2O$ [$dH_2O$]) for 24 hours at 37° C. in an atmosphere of 5% $CO_2$. E. coli DH5αF' and C600 were grown in LB medium (1% tryptone, 0.5% yeast extract, 0.5% NaCl) with aeration at 37° C. Strain DH5αF' was used to support M13 growth for sequencing and for analysis of the 1tx promoter 1acZ fusion constructs. E. coli p1tx470, p1tx332, p1tx192, p1tx135, p1tx63, ga1nP, and p652 were constructed by transformation of E. coli DH5αF' with the appropriate plasmids (see below) following established protocols (Sambrook et al., 1989, Molecular Cloning, A Laboratory Manual, Cold Spring Harbor, N.Y.).

Determination of Leukotoxic Activity.

Leukotoxic activity of intact A.a. cells was determined essentially as described (Taichman et al., 1980, Infect. Immun. 28:258–278), except that lysis of cells was visualized by staining with trypan blue. Briefly, A.a. strains were grown to late log phase in PYG medium as described above. Bacterial cells (4 ml) were washed three times in RPMI 1640 (Media Tech) and suspended in RPMI 1640 at $10^9$ cells per ml. HL60 cells (Collins et al., 1980, In: G. B. Rossi (ed.), In vivo and in vitro erythropoiesis, the Friend system, Elsevier/North Holland Biomedical Press, N.Y.) were cultured at 37° C. under 7% $CO_2$ in RPMI 1640 containing 10% fetal calf serum, 1% glutamine, 1% minimal essential medium vitamin solution (GIBCO), 1% minimal essential medium non-essential amino acid solution (GIBCO), and 50 μg of gentamicin per ml. Prior to use, HL60 cells were washed twice in RPMI 1640 to remove gentamicin and suspended in RPMI 1640 at 4×$10^6$ cells per ml.

Serial two fold dilutions of A.a. in RPMI 1640 (50 μl) were added to a microtiter plate that had been treated with 10% horse serum and washed with RPMI 1640. Subsequently, 50 μl of HL60cells were added, and the suspensions were incubated at 37° C. for 60 min. Negative controls consisted of incubating HL60 cells in RPMI 1640 without bacteria. Reactions were stopped by the addition of 100 μl of 0.4% trypan blue, and surviving cells were counted on a hemocytometer. At least four fields were counted and averaged for each dilution assayed. Percent lysis was calculated by dividing the number of surviving cells by the number of cells in the negative control.

Sequencing of the 1tx Operon.

DNA fragments flanking the JP2 1tx operon were isolated from clone λOP8 (Lally et al., 1989, J. Biol. Chem. 274:15451–15456) and cloned into M13mp18 and M13mp19 that had been cleaved with the appropriate restriction endonucleases. The promoter from strain 652 was isolated by PCR amplification of genomic DNA with oligonucleotide primers derived from the JP2 promoter sequence. Nucleotide sequencing was performed by using Sequenase version 2.0 (United States Biochemical) as specified by the manufacturer. The subsequent sequence was determined using primers derived from 1tx specific sequences. Both strands of the JP2 and 652 promoters were sequenced. Sequence analysis and comparisons with the EMBL and GenBank data bases were conducted using the Genetics Computer Group software package (Devereux et al., 1984, Nucl. Acids Res. 12:387–395).

Northern Analysis.

Total RNA was isolated from 200 ml log phase A.a. cultures following the method of Reddy et al. (1990, Bio-Techniques 8:250–251). Initially, cultures were placed on ice and 10 ml of 200 mM Tris, pH 8.0, 20 mM EDTA, 20 mM sodium azide, 20 mM aurintricarboxylic acid (Sigma Chemical Co.) was added. The cultures were centrifuged at 8,000×g for 15 min. and the cell pellet was suspended in 5 ml of STET buffer (8% sucrose, 5% Triton X-100, 5 mM EDTA, 50 mM Tris, pH 7.0, 10 mM vanadyl ribonucleoside complex) . Cell suspensions were extracted with equal volumes of phenol and chloroform, and nucleic acids were precipitated with ethanol. The nucleic acid pellet was suspended in 2 ml of dH$_2$O containing 10 mM vanadyl ribonucleoside complex and extracted and precipitated as above. The resulting pellet was suspended in 2 ml of dH$_2$O containing 1 g of CsCl, layered onto a 2.5 ml cushion of 5.7M CsCl, 0.1M EDTA, and centrifuged at 105,000×g for 18 h. The RNA pellets were then suspended in 1 ml of dH$_2$O and precipitated several times with ethanol.

For Northern analysis, 10 to 30 µg samples of RNA were electrophoresed following established procedures in 0.7% agarose gels containing 3% formaldehyde (Sambrook et al., 1989, Molecular CLoning, A Laboratory Manual, Cold Spring Harbor, N.Y.). Hybridizations were carried out with 50% formamide, 50 mM N-2-hydroxyethylpiperazine-N'-2 -ethanesulfonic acid (HEPES, pH 7.0)–0.9M NaCl, 5 mM EDTA, 100 µg of salmon sperm DNA per ml at 50° C., and filters were washed in 0.1×SSC (1×SSC is 0.15 M NaCl plus 0.015M sodium citrate) at 50° C. Blots were probed with a 470 bp fragment encompassing the JP2 1tx promoter or with a 2.5 kb fragment amplified from 1txA spanning nucleotides 644 to 3199 in the previously published 1txCA sequence (Kraig et al., 1990, Infect. Immun. 58:920–929).

Primer Extension.

Annealing reactions were carried out with 40 µg of *A.a.* RNA and 0.1 µg of end-labeled oligonucleotide a (5'-TCCATATTAAATCTCCTTGT-3) [SEQ ID NO:2] in RT buffer (50 mM Tris, pH 8.3, 40 mM KCl, 6 mM MgCl$_2$, 1 mM dithiothreitol, 0.1 mg of bovine serum albumin per ml). This oligonucleotide anneals to the region encompassing the 1txC start codon and ribosome binding site (nucleotides –15 to +5 in FIG. 1A). Samples were heated to 75° C. for 10 min, allowed to cool slowly to 25° C., and were subsequently ethanol precipitated. The dried RNA pellet was suspended in 100 µl of RT buffer containing 0.5 mM each dATP, dGTP, dCTP, and dTTP and 200 U of Moloney murine leukemia virus reverse transcriptase (Bethesda Research Laboratories). After a 2 hour incubation at 37° C., RNase A was added to a final concentration of 50 µg/ml, and incubation was continued for an additional 30 min. Samples were extracted with phenol-chloroform and precipitated with ethanol. The resulting nucleic acid pellets were suspended in 10 µl of dH$_2$O, and 2 µl of dye mix (95% formamide, 20 mM EDTA, 0.05% bromphenol blue, 0.05% xylene cyanol) was added. Reaction mixtures were heated at 75° C. for 10 min, loaded onto a 6% polyacrylamide gel, and electrchoresed for 2 to 4 hours at a constant 70 W. Dideoxy sequencing reactions (Sanger et al., 1977, Proc. Natl. Acad. Sci. USA 74:5463–5467) with the same oligonucleotide as a primer were also electrophoresed for reference. Dried gels were exposed to Kodak XAR-5 film.

Construction of JP2 Promoter Truncation Plasmids.

Fragments containing the 1tx promoter region from *A.a.* JP2 and 652 were amplified by PCR with oligonucleotide primers b and c (5α-GCA GGATCCATATTAAATCTCCTTGT-3'[SEQ ID NO:19] [+5 to –15] and 5' -GCGGTCGACAACCTGATAACAGTATT-3'[SEQ ID NO:20] [–487 to –471], respectively) The numbers in brackets indicate the site of annealing relative to the start codon of 1txC. These primers amplify a 507 bp product from JP2 genomic DNA and a 1,037 bp product from 652 genomic DNA. Amplification was carried out on a Perkin-Elmer Cetus Thermocycler with TaqI polymerase according to the protocol supplied by the manufacturer. For some experiments, the amplified fragment was cleaved at the BamHI and SalI sites specified by the oligonucleotides (underlined), extracted with phenol and chloroform, precipitated with ethanol, and suspended in TE (10 mM Tris, pH 7.5, 0.1 mM EDTA). The purified fragment was ligated to BamHI-SalI cleaved M13mp18 or M13mp19 for sequencing with T4 DNA ligase (Bethesda Research Laboratories) and transformed into *E. coli* DH5αF'.

Plasmids p1tx470, p1tx322, p1tx192, p1tx135, p1tx63, and ga1nP were constructed by using a strategy similar to that described above. Briefly, the 1acZ gene was amplified by PCR from *E. coli* C600 genomic DNA by using oligonucleotides d and e (5'-GCAGGATCCGACCATGAT TACGGATT-3'[SEQ ID NO:21] and 5'-GCGAAGCTT ACCAGACCAACTGGTAAT-3'[SEQ ID NO:22], respectively). The amplified fragment was cleaved at the BamHI and HindIII sites specified by the oligonucleotides, purified as described above, and ligated into pACYC184. Transformation of *E. coli* DH5αF' with this plasmid generated strain ga1nP. Plasmid from *E. coli* ga1nP was then used to construct a series of 1tx promoter 1acz fusion constructs. The 1tx promoter fragments of 470, 322, 192, and 135 bp were amplified from *A.a.* JP2 genomic DNA. Oligonucleotide pairs used for amplifying these fragments are 1tx470 (b and c), 1tx322, (f and c), 1tx192 (g and c), and 1tx135 (h and c), where oligonucleotides f, g, and h are 5' -CC GTCGACTAGGTAATTTATCCGG-3' [SEQ ID NO:23] (–323 to –306), 5' -CCGTCGACTATGAATACTGG AAAC-3' [SEQ ID NO:24] (–191 to –175), and 5' -CC GTCGACTAAGATTAGCACAATCG-3' [SEQ ID NO:25] (–135 to –118), respectively. Amplified fragments were digested with the appropriate restriction enzymes, ligated into ga1nP, and introduced into *E. coli* DH5αF'.

Plasmid p1tx63 was derived from p1tx470 by digestion with SphI and HindIII to generate a 3.2 kb fragment containing the entire 1acZ gene and 63 bp of the 1tx promoter region. This fragment was isolated from low melting point agarose and cloned into pACYC184 as described above. The plasmid p652 was constructed by inserting the 1,037 bp amplification product derived from strain 652 genomic DNA into ga1np as described above.

Determination of β-Galactosidase Activity.

*E. coli* strains containing the 1acZ fusion constructs were grown for 4 hours in LB medium. Cultures were centrifuged, and the cell pellets were washed and suspended in 0.1M sodium phosphate, pH 7.5, at an optical density at 600 nm (OD$_{600}$) of 0.05. Cell cultures of *E. coli* p652 and ga1nP were suspended at an OD of 0.5. β-Galactosidase activity was determined by using o-nitrophenyl-β-D-galactoside (ONPG) as follows. A 5 µl portion of cell suspension, 10 µl of 0.01% sodium dodecyl sulfate, and 25 µl of chloroform were added to 227 µl of 0.1M sodium phosphate, pH 7.5. After incubation at 25° C. for 10 min, 3 µl of Mg buffer (0.2 M MgCl$_2$, 4.5M β-mercaptoethanol) and 60 µl of ONPG (4 mg of ONPG per ml in 0.1M sodium phosphate) was added. Samples were incubated for 30 min at 37° C. Reactions were terminated by the addition of 0.5 ml of 1M Na$_2$CO$_3$, and the relative levels of β-galactosidase activity were determined by measuring the OD$_{420}$. All reactions were run in triplicate. Levels of lacZ expressed from the lac promoter were determined with *E. coli* C600 cells induced with 0.1 M lactose.

Classification of the 1tx Promoter Structure of Other *A.a.* Strains.

The distribution of the JP2 and 652 promoters was determined by Southern blotting of EcoRI digested genomic DNA using the 492 bp PCR product described above as a probe. The JP2 and 652 promoters were characterized by a 3.4 and a 3.8 kb hybridizing fragment, respectively. Some strains were also classified by PCR amplification of the 1tx promoter with oligonucleotides b and c above. These primers amplify a 492 bp fragment from JP2 and related strains and a 1,022 bp fragment from 652-like strains. The promoters from the two JP2-like strains identified by PCR were confirmed by sequencing.

Analysis of the A.a. JP2 Promoter.

To identify potential promoter sequences, we sequenced a 1.8 kb EcoRI-SmaI fragment containing approximately 1.6 kb upstream of 1txC. The nucleotide sequence of a portion of this fragment is shown in FIG. 1A. Part of this sequence (residues +5 to −493) was included in a previously published sequence of 1txCA (Kraig et al., 1990, Infect. Immun. 58:920–929). Sequences similar to E. coli consensus −10 and −35 elements are located approximately 350 bp upstream of 1txC and correspond to the putative promoter sequences identified by Kraig et al. (1990, Infect. Immun. 58:920–929). A second set of putative −10 and −35 elements, suggested by deletion and primer extension analyses is also labeled. The remainder of the EcoRI-SmaI fragment contains an ORF exhibiting 92% similarity to the E. coli glyA gene, encoding serine hydroxymethyltransferase (Plamann et al., 1983, Nucl. Acids Res. 11:2065–2075).

Interestingly, the 1tx promoter region contains a small ORF between the putative promoter elements at −350 and 1txc. This ORF is capable of encoding a 10 kDa peptide but was not identified in previously published sequences of the 1tx operon (Kraig et al., 1990, Infect. Immun. 58:920–929; Lally et al., 1989, J. Biol. Chem. 274:15451–15456). It is preceded by a ribosome binding site and terminates 22 bp upstream of 1txC. The intergenic region between the ORF and 1txC contains the ribosome binding site of 1txC, but no transcriptional termination sequence was detected, suggesting that the ORF is cotranscribed with 1txCABD. This was confirmed by Northern and primer extension analyses in the experiments described below.

As shown in FIG. 2, three mRNAs of 3.8, 4.2, and 8 kb were identified on Northern blots of JP2 RNA probed with a 2.5 kb fragment amplified from 1txA. However, the 492 bp probe containing the ORF sequence hybridized only with the 4.2 kb mRNA, an mRNA not previously identified as a specific transcript of the 1tx operon. These results indicate that the ORF region is transcribed but is present in only one of the three 1tx-specific mRNAs. In addition, primer extension reactions were conducted with an oligonucleotide which anneals to the region encompassing the 1txC start codon and ribosome binding site (−15 to +5 FIG. 1A). As shown in FIG. 3, two major primer extension products of approximately 40 and 340 bases were detected. The 340 base product is consistent with transcription being initiated at −335 (FIG. 1A) and promoted by the −10 and −35 elements previously identified by Kraig et al. (1990, Infect. Immun. 58:920–929). The smaller extension product may arise from premature termination by the reverse transcriptase, but it is also possible that transcriptional initiation occurs from a second promoter or that a primary 1tx transcript is processed posttranscriptionally.

Identification of a Second 1tx Promoter.

To determine whether a second promoter directs transcription from the 1tx operon, a series of truncations of the JP2 upstream region, shown schematically in FIG. 4A, were constructed and fused to a promoterless lacZ gene. These constructs were introduced into E. coli DH5αF', and β-galactosidase activity exhibited by these bacteria was assessed. As shown in FIG. 4B, the intact JP2 1tx promoter (p1tx470) efficiently directed lacZ expression. The promoter p1tx470 expressed approximately two to threefold lower levels of β-galactosidase than that expressed by the endogenous lacZ promoter. However, p1tx322 and the remaining three constructs, which do not possess the −10 and −35 elements identified above, also transcribed lacZ. The levels of lacZ expression directed by p1tx322 and p1tx192 were approximately twofold lower than those directed by p1tx470. Further deletions within the region between −63 and −192 resulted in an additional twofold reduction in lacZ expression. It is unlikely that vector sequences contribute to lacZ expression since ga1np, which contains only the promoterless lacZ gene, did not express significant levels of β-galactosidase activity. These results suggest that 1tx transcription may also initiate from a site immediately upstream of 1txC.

Analysis of the A.a. 652 1tx promoter.

To compare the activities of the JP2 and 652 1tx promoters, the 652 promoter region was amplified from genomic DNA. The resulting 1,022 bp fragment is larger than the 492 bp product amplified from JP2 by the same primers, suggesting that the 652 promoter differs from JP2. This fragment was inserted into ga1np to generate p652. As shown in FIG. 4B, the lacZ activity specified by p652 was significantly lower than that specified by p1tx470, even though 10 fold higher levels of p652 extract were used. Thus, the A.a. 652 promoter is significantly less active in E. coli than is the JP2 promoter. Strain 652 also expressed lower steady state levels of 1tx mRNA than did JP2 (FIG. 5). The predominant 652 1tx transcript corresponds to the JP2 3.8 kb mRNA.

To determine whether the 652 and JP2 promoters differ, the nucleotide sequence of the 652 promoter region was determined. As shown in FIG. 6, the 652 promoter is virtually identical to the JP2 promoter from nucleotides −989 to −585 and from −54 to the 1txC initiation codon. Only three single base changes were detected (G to A at positions −965 and −959; A to G at position −784). However, the 652 promoter contains a region of 530 bp which is not present in the JP2 promoter. As a result, the structure of the upstream ORF differs between the two strains. The 652 ORF is larger (encoding 150 residues) and terminates 340 bp upstream of the 1txC start codon. In addition, the −10 and −35 elements situated 350 bp upstream of 1txC in JP2 are more than 800 bp upstream of 1txC in 652.

Distribution of 652 and JP2 Promoter Structures Among A.a. Strains.

To determine the distribution of the JP2 and 652 promoter structures among isolates of A.a., a total of 96 strains representing serotypes a through e were analyzed by Southern blotting to detect the EcoRI RFLP arising from the difference in size of the two known promoters or by PCR amplification of the promoter region with oligonucleotides based on the JP2 sequence. Of these 96 strains, only 2 possessed the JP2 promoter structure, and this was confirmed by sequence analysis. These 2 strains and 13 others possessing the 652 promoter were chosen for further analysis (Table 1). To ascertain whether toxicity correlates with promoter structure within this limited sample of strains, the lytic activity of each organism against HL60 cells was determined. As shown in Table 1, strains possessing the JP2-like promoter exhibited a 50% lethal dose ($LD_{50}$) similar to that of JP2 whereas those resembling 652 expressed 10 to 20 fold lower levels of toxicity.

RFLP Diagnostic Test.

The results of the experiments described above establish clear differences between the promoter sequences which drive expression of leukotoxin in toxic and non-toxic strains of A.a. To determine whether these differences are useful in a diagnostic manner for distinguishing between toxic and non-toxic strains of A.a., Southern blot hybridization in combination with RFLP analysis was performed as described below.

Genomic DNA was isolated from *A.a.* strains JP2 and 652 using standard methods (Sambrook et al., 1989, Molecular Cloning, A Laboratory Manual, Cold Spring Harbor, N.Y.), which DNA was digested with a variety of restriction enzymes. DNA so digested was electrophoresed through 0.8% agarose gels and transferred to nitrocellulose filters. DNA contained on the filters was probed with the 492 bp promoter fragment described above which was amplified from JP2 genomic DNA and random primer labeled with $^{32}$p. The sequence of this probe is contained within FIG. 1 and spans from +5 to −487 nucleotides. Digestion of 10 µg of genomic DNA from either JP2 or 652 with EcoRI generates fragments of approximately 3.4 kb and 3.9 kb, respectively, which hybridize to the 492 bp probe. A typical Southern blot depicting this analysis is shown in FIG. 7.

A total of 96 different strains of *A.a.* have been analyzed using this test. Of these strains, two (HK909 and ER) possessed the 3.4 kb EcoRI fragment which is characteristic of the JP2 promoter. When leukotoxin activity was assessed in HK909 and ER and in thirteen of the ninety six strains tested, high levels of leukotoxin activity were evident in HK909 and ER, whereas low levels of activity were evident in the remaining thirteen strains. Thus, the presence of a 3.4 kb EcoRI fragment in the genome of a strain of *A.a.* correlates with production of high levels of leukotoxin by that strain.

PCR Diagnostic Test.

Two separate tests to identify highly toxic *A.a.* strains using PCR technology are now described below. In the first test, the entire 1tx promoter region is amplified from an unidentified sample of DNA isolated from a crude microbiological sample. The presence or absence of highly toxic strains in the test sample is determined by the presence of either a 492 bp or a 1022 bp amplification product, respectively. If both highly toxic and minimally toxic strains are present in the same test sample, amplification will result in both a 492 and a 1022 bp fragment. This test is now described in detail below.

The crude microbiological sample is obtained from the oral cavity using standard methods such as paper point sampling of the gingival crevice or curettage (scraping of dental plaque). DNA is obtained from the samples as follows: Samples are suspended in phosphate buffered saline (PBS) and are incubated at 37° C. for 20 minutes following the addition to the sample of lysozyme at a final concentration of 0.5 mg/ml. Sodium dodecyl sulfate (SDS) is added to the sample at a final concentration of 1% with thorough mixing. Samples are subsequently extracted sequentially with an equal volume of phenol saturated with PBS, and an equal volume of chloroform, followed by precipitation of the DNA in 2.5 volumes of ethanol. Alternatively, crude microbiological samples are boiled for 5 minutes following incubation with lysozyme as described above. The primers used in PCR amplification are those which are capable of annealing to nucleotides +5 to −15 and −471 to −487 of the JP2 promoter (FIG. 1A). PCR amplification of the nucleic acid samples so obtained is conducted according to standard procedures using the following reaction conditions as an example: Nucleic acid strands are separated by heating to 90°–95° C. for 0.5–5 minutes; primers are annealed to the nucleic acid at 50° –60°C. for 0.5–5 minutes; new strands are synthesized by incubation with Taq polymerase at 65°–75° C. for 0.5–5 minutes. Twenty to forty cycles are routinely performed and the products of amplification are analyzed by agarose gel electrophoresis. A typical gel is shown in FIG. 8.

A second PCR based test capable of detecting highly toxic *A.a.* is now described. For this test, collection of the microbiological samples and preparation of nucleic acids from these samples is conducted as described for the first test. The specificity of the second test for highly toxic strains of *A.a.* is derived from the design of the downstream oligonucleotide primer. This primer is designed to span the point on the JP2 sequence at which the unique 530 bp region in *A.a.* strain 652 resides (between nucleotides −54 and −55 in FIG. 1A). This region has been designated the "breakpoint" region of the JP2 promoter sequence. The upstream oligonucleotide primer used in this test is that described for the first test, i.e., a primer capable of hybridizing to −487 to −471 in the JP2 promoter region. The sequences of the breakpoint region and two of the downstream oligonucleotide primers (16 nucleotides each) which span this region are shown in FIG. 9. oligonucleotide ov1 extends one nucleotide past the break point (to residue −55) while ov4 extends 4 nucleotides past the breakpoint (to residue −58). Both ov1 and ov4 anneal to a contiguous region of 16 bases spanning the breakpoint in the JP2 promoter sequence and amplify, in conjunction with the upstream primer, fragments of 430 bp and 427 bp respectively. However, neither ov1 nor ov4 is capable of annealing to the corresponding contiguous 16 residue region of the 652 promoter since the unique 530 base pair domain interrupts this region. Thus, under the appropriate annealing conditions (described below) the 3' ends of ov1 and ov4 remain unassociated with the strain 652 DNA template and no amplification product is synthesized in the PCR reaction.

The conditions for annealing ov1 and ov4 to the appropriate template are chosen such that the primers form a stable duplex with the JP2 promoter sequence of 16 residues in length, but cannot form such a duplex with the 652 promoter sequence. Therefore, the annealing conditions are chosen to prevent the formation of a stable "loop-out" structure between the downstream primer and the 652 promoter sequence (see FIG. 10). This is accomplished by controlling the temperature of the annealing reaction. Annealing temperatures of greater than 60° C. prevent the synthesis of an amplification product using ov4 and strain 652 DNA, but this temperature has little effect on the synthesis of an amplification product using ov4 and strain JP2 DNA. Therefore, the temperature at which this test is conducted should be at least 60° C. The extent to which the downstream primer extends upstream of the breakpoint may also influence the amount of stable "loop-out" structure that forms with strain 652 DNA as a template at a given annealing template. Primers which extend farther upstream of the breakpoint than ov4 (i.e., greater than a 4 nucleotide extension) will require higher annealing temperatures to prevent the formation of stable "loop-out" structures since a longer stretch of complementary bases will be present to anneal to the region immediately upstream of the unique 530 bp domain in the 652 promoter sequence.

The downstream oligonucleotide useful in the PCR test should anneal to the region of the JP2 breakpoint and actually span the breakpoint. The 5' end of the oligonucleotide should also form a stable duplex with strain 652 DNA (i.e., it should be of sufficient length to form a stable duplex under the conditions used in the PCR test. The 3' end of the oligonucleotide should not form a stable duplex with 652 DNA under the conditions of the PCR test. Thus, preferably, the 3' end comprises no more than 5 nucleotides. Longer 3' ends are possible; however, if they are used, higher annealing temperatures should be used in the PCR reaction and such higher temperatures generally result in an overall reduction in yield of the product. Further, if the size of the 3' end approaches the size of the 5' end, they will not be distinguishable. Thus, the maximum number of nucleotides for the 3' end is preferably 5, while the minimum number of nucleotides for the 5' end is referably 8.

To assess the sensitivity of the second test, JP2 genomic DNA was mixed with 652 genomic DNA at ratios of 1:10, 1:100 and 1:1000. The samples so mixed were subjected to PCR using ov4 as the downstream oligonucleotide primer. The results are presented in FIG. 12, wherein it is apparent that no amplification product is detected using 652 DNA alone. However, a predicted 492 bp product is evident when JP2 DNA is included in the amplification reaction even when 652 genomic DNA is present in a 1000 fold excess. Further, since only 10% of the total sample was used to obtain this result, the sensitivity of the test may be greatly enhanced when a higher percent of the sample is applied to the gel.

Detection of Highly Toxic A.a. in Children with Localized Juvenile Periodontitis.

Localized juvenile periodontitis (LJP) afflicts children usually between the ages of 8 and 15 which if untreated may result in significant loss of the tissues which support the teeth. To assess the association of LJP with different strains of A.a., bacterial samples were collected from the oral cavity of both healthy and LJP children which were processed for PCR analysis as described herein. Amplification reactions using genomic DNA isolated from each sample as a template were conducted using oligonucleotide primers ov1 and ov4, or using primers which anneal to the +5 to −15 and −487 to −471 regions of the JP2 promoter (FIG. 1A). The results are summarized in Table 2.

TABLE 2

| Patient | Age | Diagnosis[1] | Aα Phenotype[2] |
|---|---|---|---|
| 23 | 14 | LJP | JP2 |
| 363 | 12 | LJP | JP2 |
| 366 | 20's | periodontitis | 652 |
| 651 | ? | LJP | JP2 |
| AJ | 9 | healthy | 652 |
| SF | 15 | LJP | JP2 |
| D13[3] | 13 | healthy | 652 |
| D1-6[4] | 15 | LJP | JP2 |
| D7[3] | 10 | healthy | 652 |
| D9[3] | 7 | healthy | 652 |
| D11[3] | 11 | healthy | 652 |
| ER | ? | LJP | JP2 |
| HK909 | ? | unknown | JP2 |
| JP2 | ? | LJP | JP2 |

[1] samples were obtained from the Univ. Penna. School of Dental Medicine and SUNY, Buffalo Dental School
[2] JP2 phenotype amplifies a 492 bp product; 652 phenotype amplifies a 1022 bp product
[3] a total of four samples from two sites were analyzed. All exhibited the 652 phenotype
[4] a total of 16 samples from 6 sites were analyzed. All exhibited the JP2 phenotype The highly toxic JP2 phenotype of A.a. was isolated from all of the individuals diagnosed as having LJP, while the non-toxic 652 strain was isolated from healthy individuals or, in one case, from an adult with periodontitis. In other healthy individuals who were also tested, no detectable levels of A.a. of any phenotype were evident. Thus, the PCR test of the invention successfully detects the highly toxic J?2 strain of A.a. in patients with LJP, demonstrating that this strain is associated with LJP. Further, the results of this study demonstrate that the PCR test is useful for diagnosis of LJP.

Kits for Detection of Highly Toxic Strains of Actinobacillus actinomycetemcomitans.

The invention further features a kit for detection of the presence of a highly toxic strain of Actinobacillus actinomycetemcomitans in a human patient. In one aspect, the kit comprises one primer which is an oligonucleotide comprising nucleotides complementary to nucleotides +5 to −15 of the Actinobacillus actinomycetemcomitans JP2 leukotoxin promoter, and another primer which is an oligonucleotide comprising nucleotides complementary to nucleotides −471 to −487 of the Actinobacillus actinomycetemcomitans JP2 leukotoxin promoter. The kit further contains Actinobacillus actinomycetemcomitans strain JP2 and strain 652 DNA, and also includes instructions for using the kit.

In another aspect, the kit is similar to that described above except that the primer comprises an oligonucleotide complementary to the Actinobacillus actinomycetemcomitans JP2/652 leukotoxin promoter breakpoint region as well as a primer comprising an oligonucleotide complementary to nucleotides −471 to −487 of the Actinobacillus actinomycetemcomitans JP2 promoter. The kit further includes Actinobacillus actinomycetemcomitans strain JP2 and strain 652 DNA, and instructions for using the kit.

In yet another aspect, the kit includes a probe capable of distinguishing between the leukotoxin promoter sequence of a highly toxic strain of Actinobacillus actinomycetemcomitans and the leukotoxin promoter sequence of a nontoxic strain of Actinobacillus actinomycetemcomitans, Actinobacillus actinomycetemcomitans strain JP2 and strain 652 DNA, and instructions for using the kit.

Expression of the JP2 Open Reading Frame in E.coli.

A small open reading frame (ORF) has been identified which is positioned immediately upstream of 1txC, which ORF has not been previously known to be associated with the 1tx operon. The ORF is preceded by a ribosome binding site but does not possess a transcriptional terminator sequence at its 3' end, indicating that the ORF is cotranscribed with the 1tx operon. That this is the case was confirmed by Northern blot hybridization analysis (FIG. 2). To assess the function of the ORF, a DNA fragment encoding the ORF was inserted into the plasmid pMM367 (Furste et al., 1986, Gene 48:119–131) such that expression of the ORF is placed under the control of the lacZ promoter. In this case, expression of the ORF may be regulated by the presence or absence of isopropylthiogalactoside (IPTG), a known inducer of the lac promoter. The chimeric plasmid so generated was introduced in E.coli DH5α cells. Expression of the ORF was assessed in the presence or absence of IPTG and the results are presented in FIG. 12. It is evident from FIG. 12 that induction of ORF expression resulted in cessation of growth of E.coli whereas no affect on cell growth was observed in the absence of expression of this ORF. These results suggest that expression of the ORF may affect E.coli cell growth which growth may be involved in regulation of expression of the 1tx operon.

To determine the effect of overexpression of ORF on 1tx expression in A.a. a fragment encoding the ORF was cloned into the E.coli/A.a. shuttle vector, pYGK, which vector was introduced into A.a. by electroporation. The plasmid pYGK was constructed by inserting a kanamycin resistance gene (obtained as a cartridge from Pharmacia) into the plasmid EcoRV site in plasmid pYG53, a derivative of the naturally occurring Actinomycetemcomitans pleuropneumoniae plasmid, pYG10 (Lalonde et al., 1989, Gene 85:243–246). Results suggest that expression of the JP2 ORF in strain 652 serves to enhance leukotoxin production somewhat, whereas, expression of the 652 ORF in JP2 reduces leukotoxin expression somewhat. These preliminary results are suggestive of a regulatory role for the ORF in leukotoxin production.

While this invention has been disclosed with reference to specific embodiments, it is apparent that other embodiments and variations of this invention may be devised by others skilled in the art without departing from the true spirit of the invention. The appended claims are intended to be construed to include all such embodiments and equivalent variations.

What is claimed is:

1. A method of determining the presence or absence of a highly toxic or non-toxic strain of *Actinobacillus actinomycetemcomitans* in a human patient comprising performing a polymerase chain reaction on DNA in a sample obtained from said patient using a first primer comprising an oligonucleotide having between about 8 and about 80 nucleotides which specifically anneals to nucleotides +5 to −15 of the *Actinobacillus actinomycetemcomitans* JP2 leukotoxin promoter and a second primer comprising an oligonucleotide having between about 8 and about 80 nucleotides which specifically anneals to nucleotides −471 to −487 of the *Actinobacillus actinomycetemcomitans* JP2 leukotoxin promoter, and comparing the resulting DNA fragment to DNA fragments generated in control reactions using JP2 and 652 zenomic DNA, wherein the presence of a DNA fragment in said polymerase chain reaction having a length similar to the fragment in the JP2 control reaction is indicative of the presence of said highly toxic strain in said sample and the presence of a DNA fragment in said polymerase chain reaction having a length similar to the fragment in the 652 control reaction is indicative of the presence of said non-toxic strain in said sample.

2. A method of determining the presence or absence of a highly toxic strain of *Actinobacillus actinomycetemcomitans* in a human patient comprising performing a polymerase chain reaction on DNA in a sample obtained from said patient using a first primer comprising an oligonucleotide having between about 8 and about 80 nucleotides which specifically anneals to the *Actinobacillus actinomycetemcomitans* JP2/652 leukotoxin promoter breakpoint region and a second primer comprising an oligonucleotide having between about 8 and about 80 nucleotides which specifically anneals to nucleotides −471 to −487 of the *Actinobacillus actinomycetemcomitans* JP2 promoter, and comparing the resulting DNA fragment to DNA fragments generated in control reactions using JP2 genomic DNA, wherein the presence in said sample of an amplification product having a length similar to the amplification product of the JP2 control reaction is indicative of the presence of said highly toxic strain and the absence in said sample of an amplification product having a length similar to the amplification product of the JP2 control reaction is indicative of the absence of said highly toxic strain.

3. An isolated purified leukotoxin promoter DNA sequence having at least about 80% homology with a DNA sequence comprising an *Actinobacillus actinomycetemcomitans* strain 652 leukotoxin promoter.

4. An *Actinobacillus actinomycetemcomitans* strain 652 leukotoxin promoter DNA sequence consisting of SEQ ID NO:9.

* * * * *

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

AACCTGATAA CAGTATT                                                              17

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

TCCATATTAA ATCTCCTTGT                                                           20

( 2 ) INFORMATION FOR SEQ ID NO:3:

( i ) SEQUENCE CHARACTERISTICS:
        ( A ) LENGTH: 234 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

ATGTCCAGTA CAGGATATGC TCCATTTTAT CTCCGTTTTA TTCAGTTCCC AAGTAATGAA               60
GTTTTACTCT ATGAATACTG GAAACTTGTT CAGAATTTTG TACAAAAGGT TAGTAAAATA              120
ACGGTAAGAT TAGCACAAAT CGTTGGCATT CTCGGCGAAA AAACTATTTG GAAATACCAA              180
AGTACTTTTA ATGATGGCAT GCTGGATATT GTGGTTTGGT TATCTTATTC AAAA                    234

( 2 ) INFORMATION FOR SEQ ID NO:4:

( i ) SEQUENCE CHARACTERISTICS:
        ( A ) LENGTH: 450 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

ATGTCCGGTA CAGAATATGC TCCATTTTAT CTCCGTTTTA TTCAGTTCCC AAGTAATGAA               60
GTTTTACTCT ATGAATACTG GAAACTTGTT CAGAATTTTG TACAAAAGGT TAGTAAAATA              120

```
ACGGTAAGAT  TAGCACAAAT  CGTTGGCATT  CTCGGCGAAA  AAACTATTTG  GAAATACCAA      180

AGTACTTTTA  ATGATGGCAT  GCTGGAAGGT  GAAGCAGCTA  AACAAGAAGT  TTCCCGCACT      240

TTAAGAAGTA  GTGCTTTACT  TGTCGCAAGT  GCCATAGTTA  TCCACTTTAA  ATCTAATTTT      300

ACCAACCTTC  TTATACTGTC  ACAGATTACA  CAATATTGTA  GACATCGCCC  TAAACCTAAA      360

AAAAGTAAAT  ACTTCCCCCT  CTACCTCTCT  TGCTTATTAC  GCAGACGATT  AACTGAATTT      420

AAAATTACCC  TTCTACCGTT  GCCATGGGGC                                          450
```

(2) INFORMATION FOR SEQ ID NO:5:

(i) SEQUENCE CHARACTERISTICS:
        (A) LENGTH: 78 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Met  Ser  Ser  Thr  Gly  Tyr  Ala  Pro  Phe  Tyr  Leu  Arg  Phe  Ile  Gln  Phe
1                  5                        10                       15

Pro  Ser  Asn  Glu  Val  Leu  Leu  Tyr  Glu  Tyr  Trp  Lys  Leu  Val  Gln  Asn
              20                       25                       30

Phe  Val  Gln  Lys  Val  Ser  Lys  Ile  Thr  Val  Arg  Leu  Ala  Gln  Ile  Val
              35                       40                       45

Gly  Ile  Leu  Gly  Glu  Lys  Thr  Ile  Trp  Lys  Tyr  Gln  Ser  Thr  Phe  Asn
         50                       55                       60

Asp  Gly  Met  Leu  Asp  Ile  Val  Val  Trp  Leu  Ser  Tyr  Ser  Lys
65                       70                       75
```

(2) INFORMATION FOR SEQ ID NO:6:

(i) SEQUENCE CHARACTERISTICS:
        (A) LENGTH: 150 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Met  Ser  Gly  Thr  Glu  Tyr  Ala  Pro  Phe  Tyr  Leu  Arg  Phe  Ile  Gln  Phe
1                  5                        10                       15

Pro  Ser  Asn  Glu  Val  Leu  Leu  Tyr  Glu  Tyr  Trp  Lys  Leu  Val  Gln  Asn
              20                       25                       30

Phe  Val  Gln  Lys  Val  Ser  Lys  Ile  Thr  Val  Arg  Leu  Ala  Gln  Ile  Val
              35                       40                       45

Gly  Ile  Leu  Gly  Glu  Lys  Thr  Ile  Trp  Lys  Tyr  Gln  Ser  Thr  Phe  Asn
         50                       55                       60

Asp  Gly  Met  Leu  Glu  Gly  Glu  Ala  Ala  Lys  Gln  Glu  Val  Ser  Arg  Thr
65                       70                       75                       80

Leu  Arg  Ser  Ser  Ala  Leu  Leu  Val  Ala  Ser  Ala  Ile  Val  Ile  His  Phe
                   85                       90                       95

Lys  Ser  Asn  Phe  Thr  Asn  Leu  Leu  Ile  Leu  Ser  Gln  Ile  Thr  Gln  Tyr
              100                      105                      110

Cys  Arg  His  Arg  Pro  Lys  Pro  Lys  Lys  Ser  Lys  Tyr  Phe  Pro  Leu  Tyr
              115                      120                      125

Leu  Ser  Cys  Leu  Leu  Arg  Arg  Leu  Thr  Glu  Phe  Lys  Ile  Thr  Leu
              130                      135                      140
```

```
        Leu  Pro  Leu  Pro  Trp  Gly
        145            150
```

(2) INFORMATION FOR SEQ ID NO:7:

(i) SEQUENCE CHARACTERISTICS:
        (A) LENGTH: 584 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 321..557

(xi) SEQUENCE DESCRIPTION: SEQ ID NO:7:

```
TAATTTTAAT  CAAATGAAAA  AAAACAAAGC  GGTAATGAAA  ATTGCCGCTT  TTTCTTTTTG   60

AGAAATATGA  CAGTCAAAAT  CTTACAGATC  AAAACCTGAT  AACAGTATTT  TCTCAGTCTA  120

ATTTTTGCGT  ATTAATACAA  TACGGGATTG  CGTAGATAAA  GTATTATCAA  AAAACTAATA  180

ATTTTATGAA  ATTAAATAAT  TTTTTCTATT  GACTATTAAA  GAATCCGGAG  TAAATTAGTC  240

TCCAAAATTA  ACCAAAACTA  GGTAATTTAT  CCGGTCAAAG  GTTATCTTAA  GTATTAACCC  300

TAAGAAAAAG  GAAAACGAGT  ATG  TCC  AGT  ACA  GGA  TAT  GCT  CCA  TTT  TAT  350
                        Met  Ser  Ser  Thr  Gly  Tyr  Ala  Pro  Phe  Tyr
                         1                 5                          10

CTC  CGT  TTT  ATT  CAG  TTC  CCA  AGT  AAT  GAA  GTT  TTA  CTC  TAT  GAA  TAC  398
Leu  Arg  Phe  Ile  Gln  Phe  Pro  Ser  Asn  Glu  Val  Leu  Leu  Tyr  Glu  Tyr
                15                      20                         25

TGG  AAA  CTT  GTT  CAG  AAT  TTT  GTA  CAA  AAG  GTT  AGT  AAA  ATA  ACG  GTA  446
Trp  Lys  Leu  Val  Gln  Asn  Phe  Val  Gln  Lys  Val  Ser  Lys  Ile  Thr  Val
           30                      35                       40

AGA  TTA  GCA  CAA  ATC  GTT  GGC  ATT  CTC  GGC  GAA  AAA  ACT  ATT  TGG  AAA  494
Arg  Leu  Ala  Gln  Ile  Val  Gly  Ile  Leu  Gly  Glu  Lys  Thr  Ile  Trp  Lys
      45                      50                       55

TAC  CAA  AGT  ACT  TTT  AAT  GAT  GGC  ATG  CTG  GAT  ATT  GTG  GTT  TGG  TTA  542
Tyr  Gln  Ser  Thr  Phe  Asn  Asp  Gly  Met  Leu  Asp  Ile  Val  Val  Trp  Leu
 60                      65                       70

TCT  TAT  TCA  AAA  TAA  ATTATTAACA  AGGAGATTTA  ATATGGA                        584
Ser  Tyr  Ser  Lys
 75
```

(2) INFORMATION FOR SEQ ID NO:8:

(i) SEQUENCE CHARACTERISTICS:
        (A) LENGTH: 78 amino acids
        (B) TYPE: amino acid
        (D) TOPOLOGY: linear (ii) MOLECULE TYPE: protein (xi) SEQUENCE DESCRIPTION: SEQ ID NO:8:

```
Met  Ser  Ser  Thr  Gly  Tyr  Ala  Pro  Phe  Tyr  Leu  Arg  Phe  Ile  Gln  Phe
 1                  5                       10                          15

Pro  Ser  Asn  Glu  Val  Leu  Leu  Tyr  Glu  Tyr  Trp  Lys  Leu  Val  Gln  Asn
                 20                      25                       30

Phe  Val  Gln  Lys  Val  Ser  Lys  Ile  Thr  Val  Arg  Leu  Ala  Gln  Ile  Val
            35                      40                       45

Gly  Ile  Leu  Gly  Glu  Lys  Thr  Ile  Trp  Lys  Tyr  Gln  Ser  Thr  Phe  Asn
       50                      55                       60

Asp  Gly  Met  Leu  Asp  Ile  Val  Val  Trp  Leu  Ser  Tyr  Ser  Lys
 65                      70                       75
```

( 2 ) INFORMATION FOR SEQ ID NO:9:

( i ) SEQUENCE CHARACTERISTICS:
        ( A ) LENGTH: 992 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 200..652

( x i ) SEQUENCE DESCRIPTION: SEQ ID NO:9:

```
TTTTTGCGTA  TTAATACAAT  ACGGAATTGC  ATAGATAAAG  TATTATCAAA  AAACTAATAA        60

TTTTATGAAA  TTAAATAATT  TTTTCTATTG  ACTATTAAAG  AATCCGGAGT  AAATTAGTCT       120

CCAAAATTAA  CCAAAACTAG  GTAATTTATC  CGGTCAAAGG  TTATCTTAAG  TATTAACCCT       180

AAGAAAAAGG  AAAACGAGT  ATG TCC GGT ACA GAA TAT GCT CCA TTT TAT CTC           232
                      Met Ser Gly Thr Glu Tyr Ala Pro Phe Tyr Leu
                        1           5                      10

CGT TTT ATT CAG TTC CCA AGT AAT GAA GTT TTA CTC TAT GAA TAC TGG              280
Arg Phe Ile Gln Phe Pro Ser Asn Glu Val Leu Leu Tyr Glu Tyr Trp
             15              20                  25

AAA CTT GTT CAG AAT TTT GTA CAA AAG GTT AGT AAA ATA ACG GTA AGA              328
Lys Leu Val Gln Asn Phe Val Gln Lys Val Ser Lys Ile Thr Val Arg
             30              35                  40

TTA GCA CAA ATC GTT GGC ATT CTC GGC GAA AAA ACT ATT TGG AAA TAC              376
Leu Ala Gln Ile Val Gly Ile Leu Gly Glu Lys Thr Ile Trp Lys Tyr
        45              50                  55

CAA AGT ACT TTT AAT GAT GGC ATG CTG GAA GGT GAA GCA GCT AAA CAA              424
Gln Ser Thr Phe Asn Asp Gly Met Leu Glu Gly Glu Ala Ala Lys Gln
 60              65                  70                  75

GAA GTT TCC CGC ACT TTA AGA AGT AGT GCT TTA CTT GTC GCA AGT GCC              472
Glu Val Ser Arg Thr Leu Arg Ser Ser Ala Leu Leu Val Ala Ser Ala
             80                  85                  90

ATA GTT ATC CAC TTT AAA TCT AAT TTT ACC AAC CTT CTT ATA CTG TCA              520
Ile Val Ile His Phe Lys Ser Asn Phe Thr Asn Leu Leu Ile Leu Ser
             95                 100                 105

CAG ATT ACA CAA TAT TGT AGA CAT CGC CCT AAA CCT AAA AAA AGT AAA              568
Gln Ile Thr Gln Tyr Cys Arg His Arg Pro Lys Pro Lys Lys Ser Lys
        110                 115                 120

TAC TTC CCC CTC TAC CTC TCT TGC TTA TTA CGC AGA CGA TTA ACT GAA              616
Tyr Phe Pro Leu Tyr Leu Ser Cys Leu Leu Arg Arg Arg Leu Thr Glu
    125                 130                 135

TTT AAA ATT ACC CTT CTA CCG TTG CCA TGG GGC TAG CTGCTATATA                   662
Phe Lys Ile Thr Leu Leu Pro Leu Pro Trp Gly
140                 145                 150

GCTATGAAGA  TCAAATCCCG  GTTTTCATTG  TAAATTTAAA  AATATATAAG  AAATAATCTG       722

AAGCCGACTT  TATTTTTACC  CAACTACGAA  TCACTCATTT  AAATTAAATA  GGTTTATTAT       782

GCAAAATAAT  AAAGCTTGAA  TATATTCCTG  TAATATAAGG  TTAAATAAGT  TATATTTCTA       842

TTTATTGTTT  AACAATAATA  ATTAAATCAT  AGTCTATTTG  ATTTCGTAAT  GAGTTTGGCA       902

TTTTCTGTCA  TGCGATCGTG  TAAGTTATTT  TGTATATTGT  GGTTTGGTTA  TCTTATTCAA       962

AATAAATTAT  TAACAAGGAG  ATTTAATATG                                           992
```

( 2 ) INFORMATION FOR SEQ ID NO:10:

( i ) SEQUENCE CHARACTERISTICS:

(A) LENGTH: 150 amino acids
(B) TYPE: amino acid
(D) TOPOLOGY: linear (ii) MOLECULE TYPE: protein (xi) SEQUENCE DESCRIPTION: SEQ ID NO:10:

| Met | Ser | Gly | Thr | Glu | Tyr | Ala | Pro | Phe | Tyr | Leu | Arg | Phe | Ile | Gln | Phe |
|---|---|---|---|---|---|---|---|---|---|---|---|---|---|---|---|
| 1 | | | | 5 | | | | | 10 | | | | | 15 | |
| Pro | Ser | Asn | Glu | Val | Leu | Leu | Tyr | Glu | Tyr | Trp | Lys | Leu | Val | Gln | Asn |
| | | | 20 | | | | 25 | | | | | 30 | | | |
| Phe | Val | Gln | Lys | Val | Ser | Lys | Ile | Thr | Val | Arg | Leu | Ala | Gln | Ile | Val |
| | | 35 | | | | | 40 | | | | | 45 | | | |
| Gly | Ile | Leu | Gly | Glu | Lys | Thr | Ile | Trp | Lys | Tyr | Gln | Ser | Thr | Phe | Asn |
| | 50 | | | | | 55 | | | | | 60 | | | | |
| Asp | Gly | Met | Leu | Glu | Gly | Glu | Ala | Ala | Lys | Gln | Glu | Val | Ser | Arg | Thr |
| 65 | | | | | 70 | | | | | 75 | | | | | 80 |
| Leu | Arg | Ser | Ser | Ala | Leu | Leu | Val | Ala | Ser | Ala | Ile | Val | Ile | His | Phe |
| | | | | 85 | | | | | 90 | | | | | 95 | |
| Lys | Ser | Asn | Phe | Thr | Asn | Leu | Leu | Ile | Leu | Ser | Gln | Ile | Thr | Gln | Tyr |
| | | | 100 | | | | | 105 | | | | | 110 | | |
| Cys | Arg | His | Arg | Pro | Lys | Pro | Lys | Lys | Ser | Lys | Tyr | Phe | Pro | Leu | Tyr |
| | | | 115 | | | | 120 | | | | | 125 | | | |
| Leu | Ser | Cys | Leu | Leu | Arg | Arg | Arg | Leu | Thr | Glu | Phe | Lys | Ile | Thr | Leu |
| | 130 | | | | | 135 | | | | | 140 | | | | |
| Leu | Pro | Leu | Pro | Trp | Gly | | | | | | | | | | |
| 145 | | | | | 150 | | | | | | | | | | |

(2) INFORMATION FOR SEQ ID NO:11:

(i) SEQUENCE CHARACTERISTICS:
(A) LENGTH: 31 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:11:

GCATGCTGGA TATTGTGGTT TGGTTATCTT A          31

(2) INFORMATION FOR SEQ ID NO:12:

(i) SEQUENCE CHARACTERISTICS:
(A) LENGTH: 31 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:12:

TTATTTTGTA TATTGTGGTT TGGTTATCTT A          31

(2) INFORMATION FOR SEQ ID NO:13:

(i) SEQUENCE CHARACTERISTICS:
(A) LENGTH: 16 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:13:

CTATAACACC AAACCA                                                                                   16

( 2 ) INFORMATION FOR SEQ ID NO:14:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

GACCTATAAC ACCAAA                                                                                   16

( 2 ) INFORMATION FOR SEQ ID NO:15:

( i ) SEQUENCE CHARACTERISTICS:
        ( A ) LENGTH: 582 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

```
TAATTTTAAT  CAAATGAAAA  AAAACAAAGC  GGTAATGAAA  ATTGCCGCTT  TTTCTTTTTG   60
AGAAATATGA  CAGTCAAAAT  CTTACAGATC  AAAACCTGAT  AACAGTATTT  TCTCAGTCTA  120
ATTTTTGCGT  ATTAATACAA  TACGGGATTG  CGTAGATAAA  GTATTATCAA  AAAACTAATA  180
ATTTTATGAA  ATTAAATAAT  TTTTCTATT   GACTATTAAA  GAATCCGGAG  TAAATTAGTC  240
TCCAAAATTA  ACCAAAACTA  GGTAATTTAT  CCGGTCAAAG  GTTATCTTAA  GTATTAACCC  300
TAAGAAAAAG  GAAAACGAGT  ATGTCCAGTA  CAGGATATGC  TCCATTTTAT  CTCCGTTTTA  360
TTCAGTTCCC  AAGTAATGAA  GTTTTACTCT  ATGAATACTG  GAAACTTGTT  CAGAATTTTG  420
TACAAAAGGT  TAGTAAAATA  ACGGTAAGAT  TAGCACAAAT  CGTTGGCATT  CTCGGCGAAA  480
AAACTATTTG  GAAATACCAA  AGTACTTTTA  ATGATGGCAT  GCTGGATATT  GTGGTTTGGT  540
TATCTTATTC  AAAATAAATT  ATTAACAAGG  AGATTTAATA  TG                      582
```

( 2 ) INFORMATION FOR SEQ ID NO:16:

( i ) SEQUENCE CHARACTERISTICS:
        ( A ) LENGTH: 997 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

```
TTTTTGCGTA  TTAATACAAT  ACGGAATTGC  ATAGATAAAG  TATTATCAAA  AAACTAATAA   60
TTTTATGAAA  TTAAATAATT  TTTTCTATTG  ACTATTAAAG  AATCCGGAGT  AAATTAGTCT  120
CCAAAATTAA  CCAAAACTAG  GTAATTTATC  CGGTCAAAGG  TTATCTTAAG  TATTAACCCT  180
AAGAAAAGG   AAAACGAGTA  TGTCCGGTAC  AGAATATGCT  CCATTTTATC  TCCGTTTTAT  240
TCAGTTCCCA  AGTAATGAAG  TTTTACTCTA  TGAATACTGG  AAACTTGTTC  AGAATTTTGT  300
ACAAAAGGTT  AGTAAAATAA  CGGTAAGATT  AGCACAAATC  GTTGGCATTC  TCGGCGAAAA  360
AACTATTTGG  AAATACCAAA  GTACTTTTAA  TGATGGCATG  CTGGAAGGTG  AAGCAGCTAA  420
ACAAGAAGTT  TCCCGCACTT  TAAGAAGTAG  TGCTTTACTT  GTCGCAAGTG  CCATAGTTAT  480
```

-continued

| | | | | | | |
|---|---|---|---|---|---|---|
| CCACTTTAAA | TCTAATTTTA | CCAACCTTCT | TATACTGTCA | CAGATTACAC | AATATTGTAG | 540 |
| ACATCGCCCT | AAACCTAAAA | AAAGTAAATA | CTTCCCCCTC | TACCTCTCTT | GCTTATTACG | 600 |
| CAGACGATTA | ACTGAATTTA | AAATTACCCT | TCTACCGTTG | CCATGGGGCT | AGCTGCTATA | 660 |
| TAGCTATGAA | GATCAAATCC | CGGTTTTCAT | TGTAAATTTA | AAAATATATA | AGAAATAATC | 720 |
| TGAAGCCGAC | TTTATTTTTA | CCCAACTACG | AATCACTCAT | TTAAATTAAA | TAGGTTTATT | 780 |
| ATGCAAAATA | ATAAAGCTTG | AATATATTCC | TGTAATATAA | GGTTAAATAA | GTTATATTTC | 840 |
| TATTTATTGT | TTAACAATAA | TAATTAAATC | ATAGTCTATT | TGATTTCGTA | ATGAGTTTGG | 900 |
| CATTTTCTGT | CATGCGATCG | TGTAAGTTAT | TTTGTATATT | GTGGTTTGGT | TATCTTATTC | 960 |
| AAAATAAATT | ATTAACAAGG | AGATTTAATA | TGGATCC | | | 997 |

(2) INFORMATION FOR SEQ ID NO:17:

(i) SEQUENCE CHARACTERISTICS:
        (A) LENGTH: 234 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

| | | | | | | |
|---|---|---|---|---|---|---|
| ATGTCCAGTA | CAGGATATGC | TCCATTTTAT | CTCCGTTTTA | TTCAGTTCCC | AAGTAATGAA | 60 |
| GTTTTACTCT | ATGAATACTG | GAAACTTGTT | CAGAATTTTG | TACAAAAGGT | TAGTAAAATA | 120 |
| ACGGTAAGAT | TAGCACAAAT | CGTTGGCATT | CTCGGCGAAA | AAACTATTTG | GAAATACCAA | 180 |
| AGTACTTTTA | ATGATGGCAT | GCTGGATATT | GTGGTTTGGT | TATCTTATTC | AAAA | 234 |

(2) INFORMATION FOR SEQ ID NO:18:

(i) SEQUENCE CHARACTERISTICS:
        (A) LENGTH: 450 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

| | | | | | | |
|---|---|---|---|---|---|---|
| ATGTCCGGTA | CAGAATATGC | TCCATTTTAT | CTCCGTTTTA | TTCAGTTCCC | AAGTAATGAA | 60 |
| GTTTTACTCT | ATGAATACTG | GAAACTTGTT | CAGAATTTTG | TACAAAAGGT | TAGTAAAATA | 120 |
| ACGGTAAGAT | TAGCACAAAT | CGTTGGCATT | CTCGGCGAAA | AAACTATTTG | GAAATACCAA | 180 |
| AGTACTTTTA | ATGATGGCAT | GCTGGAAGGT | GAAGCAGCTA | AACAAGAAGT | TTCCCGCACT | 240 |
| TTAAGAAGTA | GTGCTTTACT | TGTCGCAAGT | GCCATAGTTA | TCCACTTTAA | ATCTAATTTT | 300 |
| ACCAACCTTC | TTATACTGTC | ACAGATTACA | CAATATTGTA | GACATCGCCC | TAAACCTAAA | 360 |
| AAAAGTAAAT | ACTTCCCCCT | CTACCTCTCT | TGCTTATTAC | GCAGACGATT | AACTGAATTT | 420 |
| AAAATTACCC | TTCTACCGTT | GCCATGGGGC | | | | 450 |

(2) INFORMATION FOR SEQ ID NO:19:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

GCAGGATCCA TATTAAATCT CCTTGT                                                26

( 2 ) INFORMATION FOR SEQ ID NO:20:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

GCGGTCGACA ACCTGATAAC AGTATT                                                26

( 2 ) INFORMATION FOR SEQ ID NO:21:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

GCAGGATCCG ACCATGATTA CGGATT                                                26

( 2 ) INFORMATION FOR SEQ ID NO:22:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

GCGAAGCTTA CCAGACCAAC TGGTAAT                                               27

( 2 ) INFORMATION FOR SEQ ID NO:23:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

CCGTCGACTA GGTAATTTAT CCGG                                                  24

( 2 ) INFORMATION FOR SEQ ID NO:24:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

CCGTCGACTA TGAATACTGG AAAC                                                  24

( 2 ) INFORMATION FOR SEQ ID NO:25:

( i ) SEQUENCE CHARACTERISTICS:
  ( A ) LENGTH: 26 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:25:

CCGTCGACTA AGATTAGCAC AAATCG     26

( 2 ) INFORMATION FOR SEQ ID NO:26:

( i ) SEQUENCE CHARACTERISTICS:
  ( A ) LENGTH: 6 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:26:

Ala Phe Tyr Gly Val Ser
1               5

( 2 ) INFORMATION FOR SEQ ID NO:27:

( i ) SEQUENCE CHARACTERISTICS:
  ( A ) LENGTH: 6 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:27:

Ala Phe Tyr Glu Cys Gln
1               5

( 2 ) INFORMATION FOR SEQ ID NO:28:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:28:

AACCTGATAA CAGTATT     17

( 2 ) INFORMATION FOR SEQ ID NO:29:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:29:

TCCATATTAA ATCTCCTTGT     20